(12) United States Patent
Roseman

(10) Patent No.: US 10,023,901 B2
(45) Date of Patent: Jul. 17, 2018

(54) CHARACTERIZATION OF LYSOSOMAL ENZYMES BY CAPILLARY ZONE ELECTROPHORESIS

(71) Applicant: Shire Human Genetic Therapies, Inc., Lexington, MA (US)

(72) Inventor: Daniel Roseman, Framingham, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 0 days.

(21) Appl. No.: 15/040,174

(22) Filed: Feb. 10, 2016

(65) Prior Publication Data

US 2016/0362719 A1 Dec. 15, 2016

Related U.S. Application Data

(62) Division of application No. 14/210,058, filed on Mar. 13, 2014, now Pat. No. 9,290,793.

(60) Provisional application No. 61/779,767, filed on Mar. 13, 2013.

(51) Int. Cl.

| | |
|---|---|
| *C12N 9/16* | (2006.01) |
| *C12Q 1/44* | (2006.01) |
| *C12Q 3/00* | (2006.01) |
| *G01N 33/68* | (2006.01) |
| *G01N 27/447* | (2006.01) |
| *A61K 38/00* | (2006.01) |

(52) U.S. Cl.
CPC ............... *C12Q 1/44* (2013.01); *C12N 9/16* (2013.01); *C12Q 3/00* (2013.01); *C12Y 301/06014* (2013.01); *G01N 27/44739* (2013.01); *G01N 27/44791* (2013.01); *G01N 33/6803* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 9,290,793 B2 * | 3/2016 | Roseman | C12N 9/16 |
| 9,320,711 B2 * | 4/2016 | Natoli | A61K 9/0085 |
| 2014/0220595 A1 | 8/2014 | Roseman | |

FOREIGN PATENT DOCUMENTS

| | | |
|---|---|---|
| WO | WO-2011/163647 A2 | 12/2011 |
| WO | WO-2012/012718 A2 | 1/2012 |

OTHER PUBLICATIONS

Alahmed, Y. et al., A validated capillary electophoresis method to check for batch-to-batch consistency during recombinant human glycosylated interleukin-7 production campaigns, Journal of Pharmaceutical and Biomedical Analysis, 51(4): 882-888 (2010).
Beckman Coulter, Introduction to Capillary Electrophorese, 47 pages, no date given.
Berkowitz, S.A. et al., Rapid quantitative capillary zone electrophoresis method for monitoring the micro-heterogeneity of an intact recombinant glycoprotein, Journal of Chromatography, 1079(1-2): 254-265 (2005).
Carvalho, A.Z. et al., Capillary zone electrophoresis method development for the analysis of Hippeastrum hybrid agglutinin samples, Journal of Chromatography B: Biomedical Sciences and Applications, 877(5-6): 563-567 (2009).
Chiari, M. et al., Analysis of Mandelonitrile Lyase and Beta-Glucosidase from Sweet Almonds by Combined Electrophoretic Techniques, Electrophoresis, 18(11): 2050-2054 (1997).
Felten, C. and Salas Solano, O., Capillary Electrophoresis in Quality Control: Part I: Application for Therapeutic Proteins, Beckman Coulter, pp. 1-8 (2010).
Friedberg, M. et al., Analysis of urinary N-acetyl-beta-glucosaminidase by capillary zone electrophoresesis, Journal of Chromatography B: Biomedical Sciences & Applications, 695(1): 187-191 (1997).
Graham, F.L. et al., Characteristics of a Human Cell Line Transformed by DNA from Human Adenovirus Type 5, Journal of General Virology, 36:59-72 (1977).
Mather, J.P. et al., Culture of testicular cells in hormone-supplemented serum-free medium, Annals of the New York Academy of Sciences, 383:44-68 (1982).
Mather, Jennie P., Establishment and Characterization of Two Distinct Mouse Testicular Epithelial Cell Lines, Biology of Reproduction, 23:243-251 (1980).
Meyers, E. and Miller, W., Optimal alignments in linear space, CABIOS, 4:1-13 (1989).
Michaels, D., et al., Imaged Capillary Isoelectric Focusing for Charge-Vairant Analysis of Biopharmaceuticals, BioProcess International, 48-52 (2011).
Roseman, D.S. et al., Quantitative capillary zone electrophoresis method for the precise determination of charge differences arising from the manufacture of heparan-N-sulfatase, Journal of Pharmaceutical and Biomedical Analysis, 85: 67-73 (2013).
Santos, Marcia R., Analysis of Monoclonal Antibody Charge Variants by Capillary Zone Electrophoresis, Beckman Coulter, pp. 1-8 (2012).
Toroian, D. and Price, P.A., The essential role of fetuin in the serum-induced calcification of collagen, Calcified Tissue International, 82(2):116-126 (2008).
Urlaub, G. and Chasin, L., Isolation of Chinese hamster cell mutants deficient in dihydrofolate reductase activity, Proceedings of the National Academy of Sciences USA, 77:4216-4220 (1980).

(Continued)

Primary Examiner — Ralph J Gitomer
(74) Attorney, Agent, or Firm — Proskauer Rose LLP; Fangli Chen; Kimberly A. Reynolds

(57) ABSTRACT

The present invention provides, among other things, methods for the characterization of recombinant Heparan N-Sulfatase (HNS) during manufacture. The present invention uses capillary zone electrophoresis to determine the charge profile, isoform distribution, and/or glycan profile of recombinant HNS; and represents a quality feature for the batch consistency, storage stability, biological half-life, pharmacokinetic, pharmacodynamic and biological activity of the enzyme. In particular, such characterization methods may be beneficial to optimize conditions and ensure consistency for the manufacture of HNS for the treatment of a patient diagnosed with Sanfilippo syndrome using enzyme replacement therapy.

20 Claims, 23 Drawing Sheets

(56) References Cited

OTHER PUBLICATIONS

Yim, K. et al., Capillary zone electrophoretic resolution of recombinant human bone morphogenetic protein 2 glycoforms an investigation into the separation mechanisms for an exquisite separation, Journal of Chromatography, 716(1): 401-412 (1995).

Zhang, L. et al., Capillary Zone Electrophoresis Method for a Highly Glycosylated and Sialylated Recombinant Protein: Development, Characterization and Application for Process Development, Analytical Chemistry, 87:470-476 (2015).

* cited by examiner

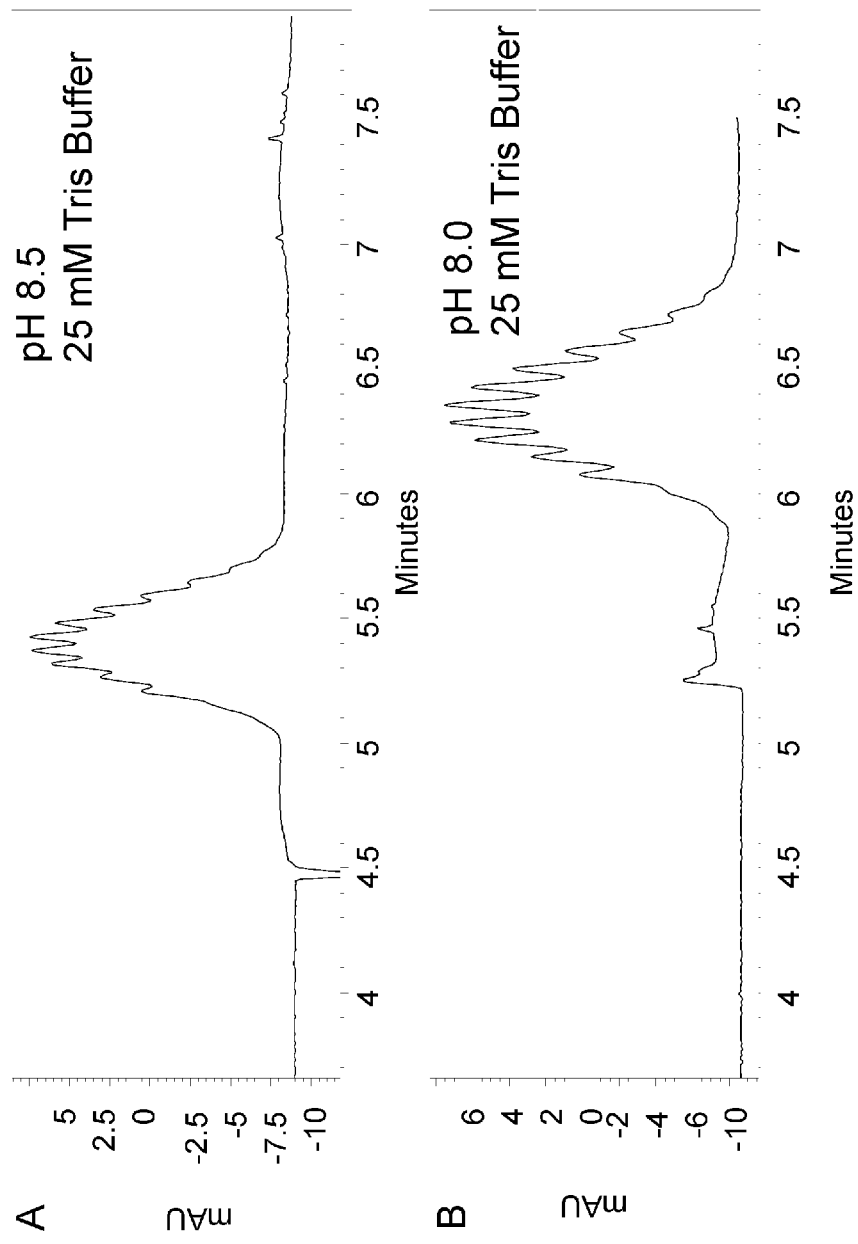
FIG. 4 A-B

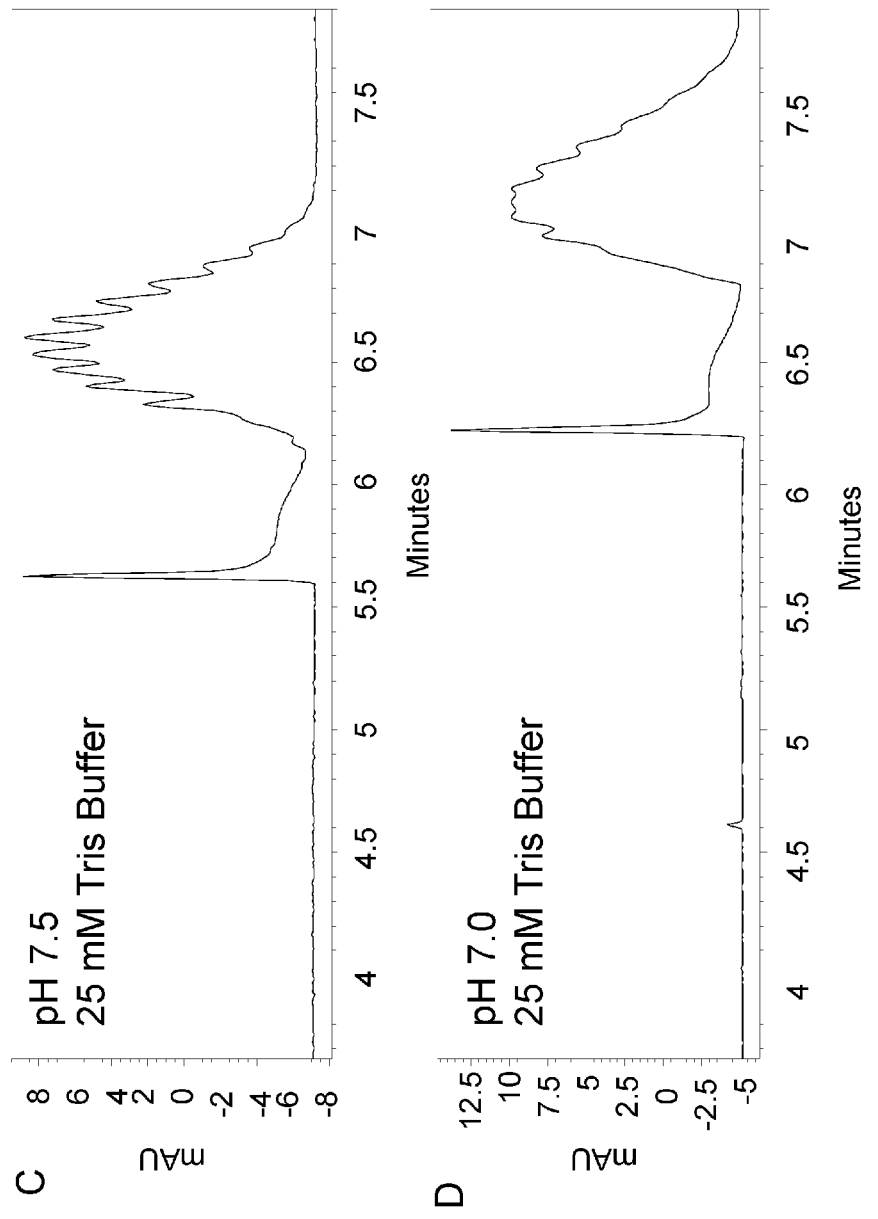
FIG. 4 C-D

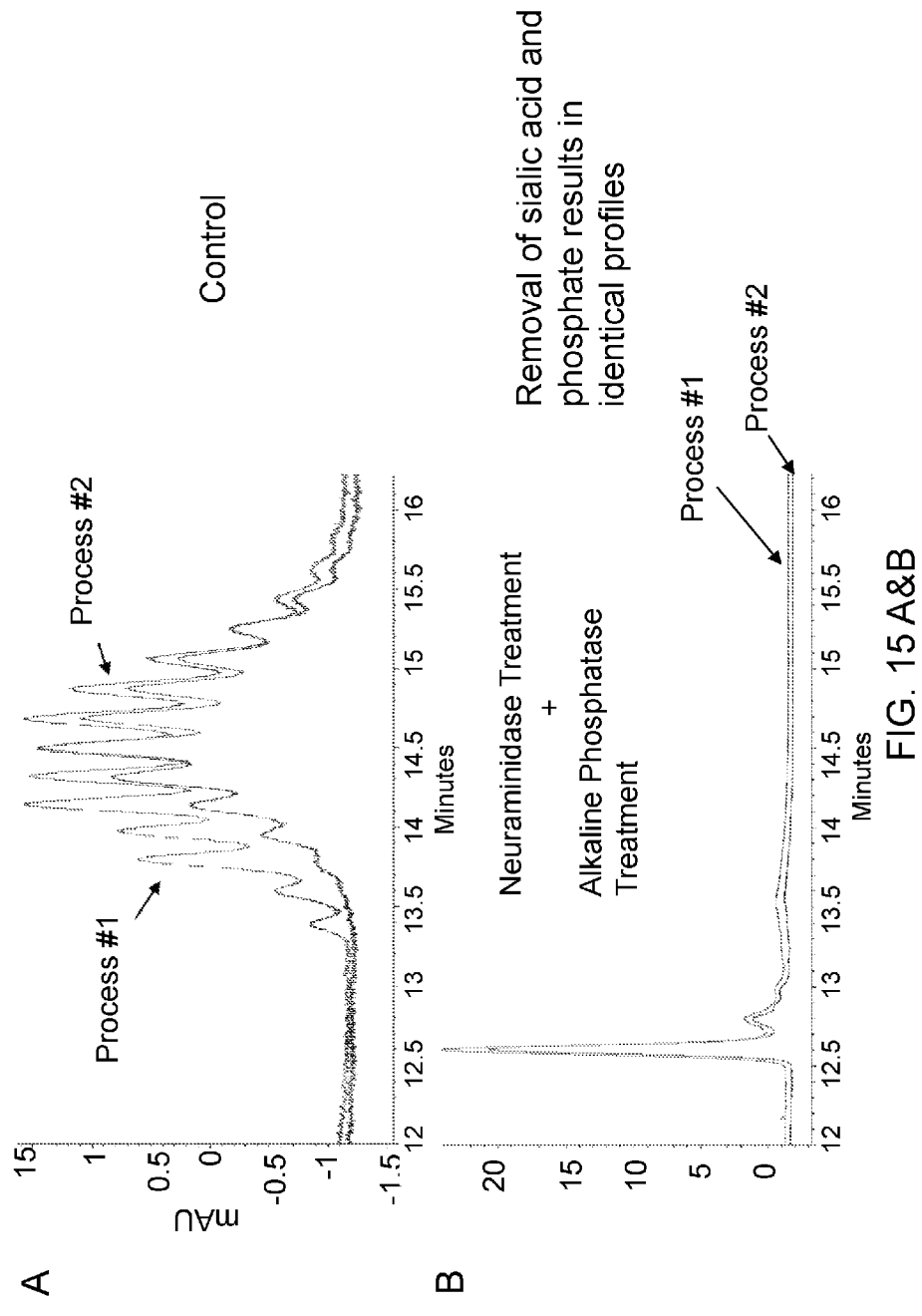
FIG. 15 A&B

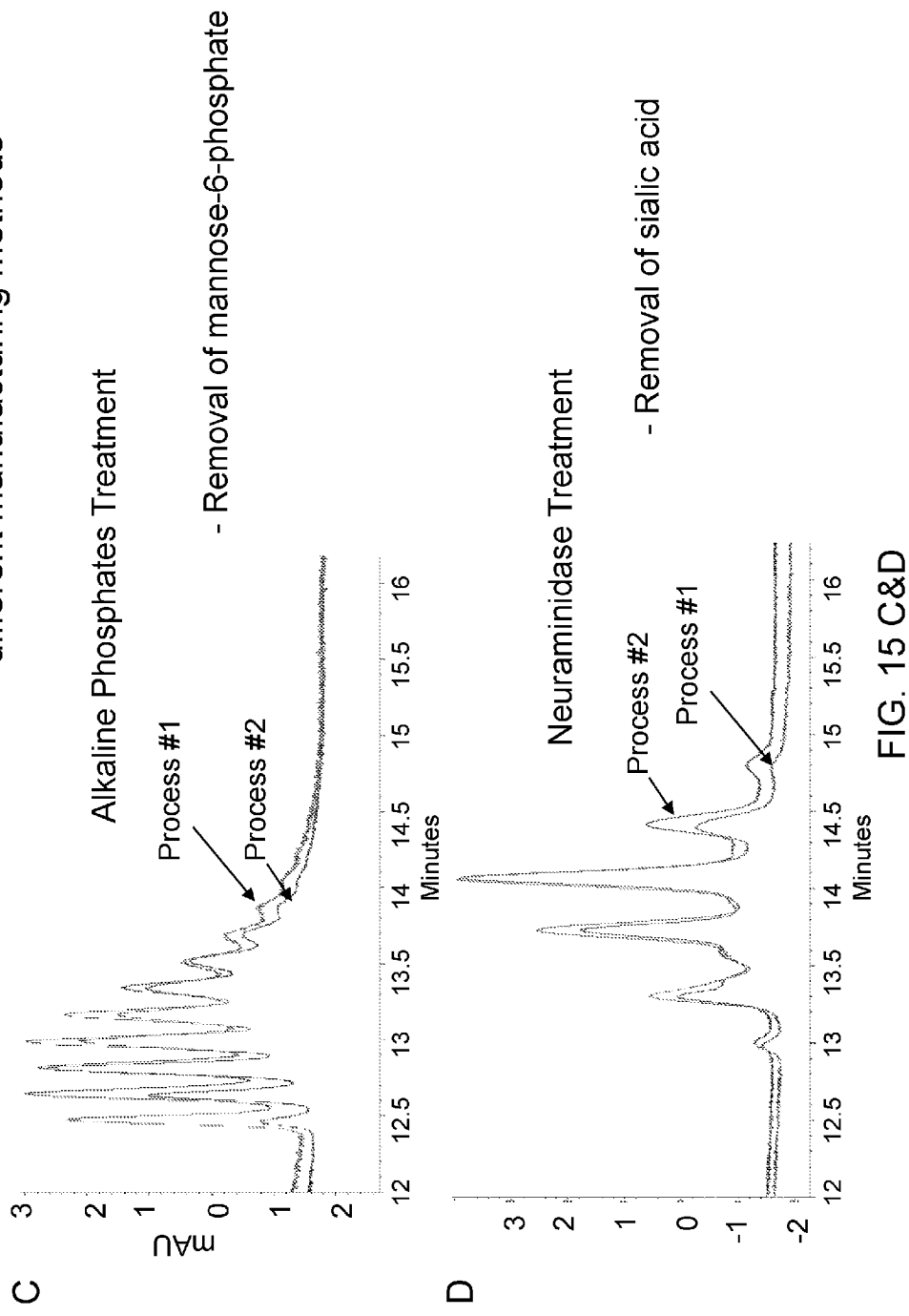
FIG. 15 C&D

SEQUENCE LISTING

<160> NUMBER OF SEQ ID NOS: 3

<210> SEQ ID NO 1
<211> LENGTH: 482
<212> TYPE: PRT
<213> ORGANISM: Homo sapiens

```
<400> SEQUENCE: 1

Arg Pro Arg Asn Ala Leu Leu Leu Ala Asp Asp Gly Gly Phe Glu
1               5                   10                  15

Ser Gly Ala Tyr Asn Asn Ser Ala Ile Ala Thr Pro His Leu Asp Ala
            20                  25                  30

Leu Ala Arg Arg Ser Leu Leu Phe Arg Asn Ala Phe Thr Ser Val Ser
        35                  40                  45

Ser Cys Ser Pro Ser Arg Ala Ser Leu Leu Thr Gly Leu Pro Gln His
50                  55                  60

Gln Asn Gly Met Tyr Gly Leu His Gln Asp Val His His Phe Asn Ser
65                  70                  75                  80

Phe Asp Lys Val Arg Ser Leu Pro Leu Leu Leu Ser Gln Ala Gly Val
                85                  90                  95

Arg Thr Gly Ile Ile Gly Lys Lys His Val Gly Pro Glu Thr Val Tyr
                100                 105                 110

Pro Phe Asp Phe Ala Tyr Thr Glu Glu Asn Gly Ser Val Leu Gln Val
            115                 120                 125

Gly Arg Asn Ile Thr Arg Ile Lys Leu Leu Val Arg Lys Phe Leu Gln
130                 135                 140

Thr Gln Asp Asp Arg Pro Phe Phe Leu Tyr Val Ala Phe His Asp Pro
145                 150                 155                 160

His Arg Cys Gly His Ser Gln Pro Gln Tyr Gly Thr Phe Cys Glu Lys
                165                 170                 175

Phe Gly Asn Gly Glu Ser Gly Met Gly Arg Ile Pro Asp Trp Thr Pro
            180                 185                 190

Gln Ala Tyr Asp Pro Leu Asp Val Leu Val Pro Tyr Phe Val Pro Asn
        195                 200                 205

Thr Pro Ala Ala Arg Ala Asp Leu Ala Ala Gln Tyr Thr Thr Val Gly
210                 215                 220

Arg Met Asp Gln Gly Val Gly Leu Val Leu Gln Glu Leu Arg Asp Ala
225                 230                 235                 240

Gly Val Leu Asn Asp Thr Leu Val Ile Phe Thr Ser Asp Asn Gly Ile
                245                 250                 255

Pro Phe Pro Ser Gly Arg Thr Asn Leu Tyr Trp Pro Gly Thr Ala Glu
            260                 265                 270

Pro Leu Leu Val Ser Ser Pro Glu His Pro Lys Arg Trp Gly Gln Val
        275                 280                 285

Ser Glu Ala Tyr Val Ser Leu Leu Asp Leu Thr Pro Thr Ile Leu Asp
290                 295                 300

Trp Phe Ser Ile Pro Tyr Pro Ser Tyr Ala Ile Phe Gly Ser Lys Thr
305                 310                 315                 320

Ile His Leu Thr Gly Arg Ser Leu Leu Pro Ala Leu Glu Ala Glu Pro
                325                 330                 335

Leu Trp Ala Thr Val Phe Gly Ser Gln Ser His His Glu Val Thr Met
            340                 345                 350

Ser Tyr Pro Met Arg Ser Val Gln His Arg His Phe Arg Leu Val His
        355                 360                 365

Asn Leu Asn Phe Lys Met Pro Phe Pro Ile Asp Gln Asp Phe Tyr Val
370                 375                 380

Ser Pro Thr Phe Gln Asp Leu Leu Asn Arg Thr Thr Ala Gly Gln Pro
385                 390                 395                 400

Thr Gly Trp Tyr Lys Asp Leu Arg His Tyr Tyr Arg Ala Arg Trp
                405                 410                 415
```

```
Glu Leu Tyr Asp Arg Ser Arg Asp Pro His Glu Thr Gln Asn Leu Ala
            420                 425                 430

Thr Asp Pro Arg Phe Ala Gln Leu Leu Glu Met Leu Arg Asp Gln Leu
            435                 440                 445

Ala Lys Trp Gln Trp Glu Thr His Asp Pro Trp Val Cys Ala Pro Asp
450                 455                 460

Gly Val Leu Glu Glu Lys Leu Ser Pro Gln Cys Gln Pro Leu His Asn
465                 470                 475                 480

Glu Leu

<210> SEQ ID NO 2
<211> LENGTH: 502
<212> TYPE: PRT
<213> ORGANISM: Homo sapiens

<400> SEQUENCE: 2

Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Leu Ala Asp Asp
            20                  25                  30

Gly Gly Phe Glu Ser Gly Ala Tyr Asn Asn Ser Ala Ile Ala Thr Pro
        35                  40                  45

His Leu Asp Ala Leu Ala Arg Arg Ser Leu Leu Phe Arg Asn Ala Phe
    50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
        275                 280                 285

Gly Thr Ala Glu Pro Leu Leu Val Ser Ser Pro Glu His Pro Lys Arg
    290                 295                 300
```

```
Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
        435                 440                 445

Gln Asn Leu Ala Thr Asp Pro Arg Phe Ala Gln Leu Leu Glu Met Leu
450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu
            500

<210> SEQ ID NO 3
<211> LENGTH: 2683
<212> TYPE: DNA
<213> ORGANISM: Homo sapiens

<400> SEQUENCE: 3
atgagctgcc ccgtgcccgc ctgctgcgcg ctgctgctag tcctgggggct ctgccgggcg    60 cgtccccgga acgcactgct gctcctcgcg gatgacggag gctttgagag tggcgcgtac   120
aacaacagcg ccatcgccac cccgcacctg acgccttgg cccgccgcag cctcctcttt   180
cgcaatgcct tcacctcggt cagcagctgc tctcccagcc gcgccagcct cctcactggc   240
ctgccccagc atcagaatgg gatgtacggg ctgcaccagg acgtgcacca cttcaactcc   300
ttcgacaagg tgcggagcct gccgctgctg ctcagccaag ctggtgtgcg cacaggcatc   360
atcgggaaga agcacgtggg gccggagacc gtgtacccgt ttgactttgc gtacacggag   420
gagaatggct ccgtcctcca ggtggggcgg aacatcacta gaattaagct gctcgtccgg   480
aaattcctgc agactcagga tgaccggcct ttcttcctct acgtcgcctt ccacgacccc   540
caccgctgtg ggcactccca gccccagtac ggaaccttct gtgagaagtt tggcaacgga   600
gagagcggca tgggtcgtat cccagactgg acccccagg cctacgaccc actggacgtg   660
ctggtgcctt acttcgtccc caacaccccg gcagcccgag ccgacctggc cgctcagtac   720
accaccgtcg gccgcatgga ccaaggagtt ggactggtgc tccaggagct gcgtgacgcc   780
ggtgtcctga cgacacact ggtgatcttc acgtccgaca cgggatccc cttccccagc   840 ggcaggacca acctgtactg gccgggcact gctgaaccct actggtgtc atccccggag   900 cacccaaaaac gctggggcca agtcagcgag gcctacgtga gcctcctaga cctcacgccc   960
```

```
accatcttgg attggttctc gatcccgtac cccagctacg ccatctttgg ctcgaagacc    1020
atccacctca ctggccggtc cctcctgccg gcgctggagg ccgagcccct ctgggccacc    1080
gtctttggca gccagagcca ccacgaggtc accatgtcct accccatgcg ctccgtgcag    1140
caccggcact tccgcctcgt gcacaacctc aacttcaaga tgcccttcc catcgaccag     1200
gacttctacg tctcacccac cttccaggac ctcctgaacc gcaccacagc tggtcagccc    1260
acgggctggt acaaggacct ccgtcattac tactaccggg cgcgctggga gctctacgac    1320
cggagccggg accccacga gacccagaac ctggccaccg acccgcgctt tgctcagctt     1380
ctggagatgc ttcgggacca gctggccaag tggcagtggg agaccacga cccctgggtg     1440
tgcgcccccg acggcgtcct ggaggagaag ctctctcccc agtgccagcc cctccacaat    1500
gagctgtgac catcccagga ggcctgtgca cacatcccag gcatgtccca gacacatccc    1560
acacgtgtcc gtgtggccgg ccagcctggg gagtagtggc aacagcccttt ccgtccacac   1620
tcccatccaa ggagggttct tccttcctgt ggggtcactc ttgccattgc ctggagggg    1680
accagagcat gtgaccagag catgtgccca gcccctccac caccaggggc actgccgtca    1740
tggcagggga cacagttgtc cttgtgtctg aaccatgtcc cagcacggga attctagaca    1800
tacgtggtct gcggacaggg cagcgccccc agcccatgac aagggagtct tgttttctgg    1860
cttggtttgg ggacctgcaa atgggaggcc tgaggccctc ttcaggcttt ggcagccaca    1920
gatacttctg aacccttcac agagagcagg caggggcttc ggtgccgcgt gggcagtacg    1980
caggtcccac cgacactcac ctgggagcac ggcgcctggc tcttaccagc gtctggccta    2040
gaggaagcct ttgagcgacc tttgggcagg tttctgcttc ttctgttttg ccccatggtc    2100
aagtccctgt tccccaggca ggtttcagct gattggcagc aggctccctg agtgatgagc    2160
ttgaacctgt ggtgtttctg ggcagaagct tatctttttt gagagtgtcc gaagatgaag    2220
gcatggcgat gcccgtcctc tggcttgggt taattcttcg gtgacactgg cattgctggg    2280
tggtgatgcc cgtcctctgg cttgggttaa ttcttcggtg acactggcgt tgctgggtgg    2340
caatgcccat cctctgcctt gggttaattc ttcggtgaca ctggcgttgc tgggtggcga    2400
tgcccgtcct ctggcttggg ttaattcttg gatgacgtcg gcgttgctgg gagaatgtgc    2460
cgttcctgcc ctgcctccac ccacctcggg agcagaagcc cggcctggac accctcggc    2520
ctggacaccc ctcgaaggag agggcgcttc cttgagtagg tgggctcccc ttgccttcc    2580
ctccctatca ctccatactg gggtgggctg gaggaggcca caggccagct attgtaaaag    2640
cttttattt tagtaaaata tacagaagtt cttttctga aaa                       2683
```

US 10,023,901 B2

CHARACTERIZATION OF LYSOSOMAL ENZYMES BY CAPILLARY ZONE ELECTROPHORESIS

RELATED APPLICATIONS

This application is a divisional application of U.S. Pat. No. 9,290,793, filed Mar. 13, 2014, which claims priority to U.S. Provisional Application Ser. No. 61/779,767 filed Mar. 13, 2013, the disclosure of each of which is hereby incorporated by reference.

SEQUENCE LISTING

The instant application contains a sequence listing which has been submitted electronically in ASCII format and is hereby incorporated by reference in its entirety. Said ASCII copy, created on Feb. 9, 2016 is named 2006685-1361_SL.txt and is 12,397 bytes in size.

BACKGROUND

Heparan N-Sulfatase (HNS) is a lysosomal enzyme involved in the degradation of heparan sulfate. A genetic defect resulting in the deficiency of this enzyme is known as mucopolysaccharidosis type IIIA or Sanfilippo disease type A. This rare autosomal recessive disease occurs in 1 of 24,000 live births, with no approved medical treatment available. Enzyme Replacement Therapy (ERT), is currently being clinically evaluated in which the recombinant form of the exogenous enzyme is introduced into a subject, to remedy an enzyme deficiency resulting from genetic mutation. In particular, recombinant HNS enzyme may be introduced into a patient diagnosed with Sanfilippo disease type A, to facilitate the degradation and biological turn-over of heparan sulfate. For the treatment, recombinant HNS glycoprotein is typically produced using a cell based expression system. Typically, the recombinant enzyme is a 54.7 kDa glycoprotein containing 5 potential N-glycosylation sites, along with several additional sites for post-translation modification. Some of these modification structures, such as those bearing terminal mannose-6-phosphate, are important for bio-efficacy while others may have roles in protein stability and/or solubility. As such, the diversity of different glycoforms present in the final recombinant product, which is influenced by both the upstream cell culture and downstream purification processes, can greatly impact the potential efficacy, pharmacodynamic and pharmacokinetic parameters of the therapeutic enzyme.

The production of recombinant protein therapeutics in a commercial setting thus typically requires control of the manufacturing processes which involves a battery of sensitive analytical methodologies to elucidate the physiochemical properties and monitor the purity, stability, and/or activity of the products. The ability to detect subtle physiochemical differences between purified batches is important towards achieving a controlled, reliable production process as well as a consistent, safe and efficacious product.

SUMMARY OF THE INVENTION

The present invention provides, among other things, improved methods to elucidate important physiochemical properties of recombinant heparan N-sulfatase (HNS) protein, permitting more effective monitoring and controlling of the quality, purity, and stability of the products produced by commercial manufacturing processes. Thus, the present invention allows more reliable production processes as well as consistent, safe and efficacious products for effective enzyme replacement therapy for Sanfilippo syndrome type A.

In part, the present invention is based on the discovery that capillary zone electrophoresis can be used to accurately characterize physiochemical properties of recombinant protein encoding an enzyme associated with a lysosomal storage disease. In some specific embodiments, the recombinant protein encodes an HNS enzyme. It is contemplated that one physicochemical property, the molecular charge of the lysosomal enzyme (i.e., HNS protein), is a particularly important attribute. The degree of charge micro-heterogeneity can arise from modifications in protein structure (i.e. deamidation) and/or the carbohydrate moieties linked to the polypeptide chain. Importantly, the degree of molecular charge (i.e. charged carbohydrate structures) has been shown to have a significant impact on a HNS protein's bio-efficacy and serum half-life as well as protein antigenicity, solubility, and protease resistance. Therefore, the quantitative analysis and characterization of native-charge heterogeneity of recombinant lysosomal enzymes, such as HNS, is an important part of product development.

A number of different analytical techniques for monitoring native-charge heterogeneity including ion exchange chromatography (IEX-HPLC), gel electrophoresis isoelectric focusing (gel-IEF), capillary isoelectric focusing (cIEF), imaged cIEF, and capillary zone electrophoresis (CZE), are known. While each of these techniques offers strengths and weaknesses, the best method for resolving charge heterogeneity of a given protein is determined on a case-by-case basis. As described in the Examples section below, the present invention demonstrates that capillary zone electrophoresis is particularly well suited to characterize the native-charge and glycan profiles for lysosomal enzymes, such as HNS, offering a high level of reproducibility and robustness over a range of assay conditions. Thus, the present invention allows for standardization and optimization of commercial production of any lysosomal enzyme. For an example, such an approach may be used to specifically recombinant HNS protein. Although the HNS protein was used as an example for the CZE analysis described in the Examples, it is contemplated that the present invention may be applied to any lysosomal enzymes.

In one aspect, the present invention provides a method of analyzing a lysosomal enzyme, such as the heparan N-sulfatase protein, comprising characterizing charge profile of enzyme by capillary zone electrophoresis. In some embodiments, the lysosomal enzyme is recombinantly produced. In some embodiments, the characterization step comprises a step of separating peak groups corresponding to charge variation, by capillary zone electrophoresis.

In some embodiments, the charge profile comprises less than 14 peak groups corresponding to the presence of charge variants. In some embodiments, the charge profile comprises 1, 2, 3, 4, 5, 6, 7, 8, 9, 10, 11, 12, or 13 peak groups corresponding to the presence of charge variants. In some embodiments, the charge profile comprises at least 14 peak groups corresponding to the presence of charge variants. In some embodiments, the charge profile comprises at least 14, 15, 16, 17, 18, 19, 20 or 21 groups corresponding to the presence of charge variants. In some embodiments, the peak groups correspond to the charge variants associated with the absence, presence or varying amount of sialic acid. In some embodiments, the peak groups correspond to the charge variants associated with the absence, presence or varying amount of mannose 6-phosphate (M6P). In some embodiments, the peak groups correspond to the charge variants associated with the absence, presence or varying amount of sialic acid and/or mannose 6-phosphate.

In some embodiments, the characterizing step comprises quantitatively determining relative migration time of each peak group. In some embodiments, the characterizing step comprises quantitatively determining relative peak area for each peak group. In some embodiments, the characterization step comprises quantitatively determining relative migration time and/or relative peak area of each peak group. In some embodiments, the relative migration time of each peak group is determined relative to an electroosmotic flow (EOF) marker. In some embodiments, more than one EOF marker is used. In some embodiments, relative peak area of each peak group is calculated by peak area percentage as compared to the total peak area.

In some embodiments, the method further comprises determining the total sialic acid content based on the charge profile. In some embodiments, the method further comprises determining the total mannose 6-phosphate content based on the charge profile. In some embodiments, the method further comprises determining the total sialic acid and/or mannose 6-phosphate content based on the charge profile. In some embodiments, the method of determining the sialic acid content comprises determining the absence, presence or amount of mono-, di- and/or tri-sialylated glycans. In some embodiments, the method of determining the M6P content comprises determining the absence, presence or amount of mono- and/or di-M6P.

In some embodiments, the method further comprises determining the quality of the lysosomal enzyme, for example HNS protein, recombinantly produced. In some embodiments, protein quality is determined at the start of manufacturing production. In some embodiments, lysosomal enzyme quality is determined at one or more times during production. In some embodiments, lysosomal enzyme quality is determined during different phases and/or steps of production. In some embodiments, lysosomal enzyme quality is determined to monitor progression, variation and/or deviations in a production process.

In some embodiments, recombinant lysosomal enzyme protein is produced using a cell culture system. In some specific embodiments, the lysosomal enzyme is HNS. In some embodiments, the cell culture system uses mammalian cells. In some embodiments, the mammalian cells used are human cells. In some embodiments, recombinant lysosomal enzyme is produced at a micro scale production rate. In some embodiments, lysosomal enzyme is produced at a midrange production scale. In some embodiments, lysosomal enzyme is produced at a large scale production rate.

In some embodiments, the method comprises determining if there is variation in the charge profile of a recombinant lysosomal enzyme, i.e. HNS, during production. In some embodiments, variation in charge profile is identified by determining enzyme charge profile at the start of production. In some embodiments, variation in charge is identified by determining enzyme charge at one or more times during manufacture. In some embodiments, variation in charge is identified by determining enzyme charge profile at the end of production. In some embodiments, variation in enzyme charge profile is determined by comparing protein charge profiles collected at one or more times during manufacture. In some embodiments, variation in lysosomal enzyme charge profile is determined by comparing protein charge profiles collected from one or more batches of enzyme produced using the same manufacturing method. In some embodiments, variation in enzyme charge profile is determined by comparing protein charge profiles collected from one or more lots of enzyme produced within the same manufacturing batch. In some embodiments, variation in enzyme charge profile is determined by comparing protein charge profiles collected from one or more batches of enzyme produced using a different manufacturing method.

In some embodiments, the method comprises determining if there is variation in the charge profile of a recombinant lysosomal enzyme protein as compared to a reference. In some embodiments, the reference is a charge profile for an enzyme associated with a lysosomal storage disease. In some embodiments, the references is an average charge profile for one or more different enzymes associated with a lysosomal storage disease. In some embodiments, the reference is an HNS charge profile from an HNS protein produced from a different commercial batch. In some embodiments, the reference is an HNS charge profile from HNS proteins assayed from two or more different lots, within the same commercial batch. In some embodiments, the reference is an HNS charge profile from an FDA approved product. In some embodiments, the reference is an average HNS charge profile generated from an HNS protein assayed from one or more lots and/or batches from the same commercial manufacturing process. In some embodiments, the reference is an average HNS charge profile generated from an HNS protein assayed from one or more lots and/or batches from different commercial manufacturing processes.

In some embodiments, variation in charge profile is identified by determining a HNS charge profile at the start of production. In some embodiments, variation in charge is identified by determining HNS charge at one or more different times during manufacture. In some embodiments, variation in charge is identified by determining HNS charge profile at the end of production. In some embodiments, variation in HNS charge profile is determined by comparing HNS charge profiles collected at one or more times during manufacture. In some embodiments, variation in HNS charge profile is determined by comparing HNS charge profiles collected from one or more batches of HNS enzyme produced using the same manufacturing method. In some embodiments, variation in HNS charge profile is determined by comparing HNS charge profiles collected from one or more lots of HNS enzyme produced within the same manufacturing batch. In some embodiments, variation in HNS charge profile is determined by comparing HNS charge profiles collected from one or more batches of HNS enzyme produced using the same manufacturing method.

In some embodiments, the method comprises determining a variation in charge isoform number of a recombinant lysosomal enzyme protein as compared to a reference. In some embodiments, the reference is a charge isoform number obtained by CZE, for an enzyme associated with a lysosomal storage disease. In some embodiments, the reference is an enzyme charge isoform number obtained by CZE, from a different commercial batch. In some embodiments, the reference is an average enzyme charge isoform number obtained by CZE, from two or more different lots, within the same commercial batch. In some embodiments, the reference is an enzyme charge isoform number from an FDA approved product. In some embodiments, the reference is an average enzyme charge isoform number generated from one or more lots and/or batches from the same commercial manufacturing process. In some embodiments, the reference is an average enzyme charge isoform number generated from one or more lots and/or batches from different commercial manufacturing processes.

In some embodiments, the method comprises determining a variation in charge isoform number of a recombinant HNS protein as compared to a reference. In some embodiments, the reference is a charge isoform number obtained by CZE, for an enzyme associated with a lysosomal storage disease. In some embodiments, the reference is an HNS charge isoform number obtained by CZE, from a different commercial batch. In some embodiments, the reference is an average HNS charge isoform number obtained by CZE, from two or more different lots, within the same commercial batch. In some embodiments, the reference is an HNS charge isoform number from an FDA approved product. In some embodiments, the reference is an average HNS charge isoform number generated from one or more lots and/or batches from the same commercial manufacturing process. In some embodiments, the reference is an average HNS charge isoform number generated from one or more lots and/or batches from different commercial manufacturing processes.

In some embodiments, variation in charge isoform number is identified by determining an enzyme charge profile at the start of production. In some embodiments, variation in charge is identified by determining an enzyme charge isoform number at one or more times during manufacture. In some embodiments, variation in charge is identified by determining an enzyme charge isoform number at the end of production. In some embodiments, variation in enzyme HNS charge profile is determined by comparing an enzyme charge isoform numbers collected at one or more times during manufacture. In some embodiments, variation in an enzyme charge profile is determined by comparing enzyme charge isoform numbers collected from one or more batches of enzyme produced using the same manufacturing method. In some embodiments, variation in an enzyme charge isoform number is determined by comparing enzyme charge profiles collected from one or more lots of enzyme produced within the same manufacturing batch. In some embodiments, variation in enzyme charge isoform number is determined by comparing enzyme charge profiles collected from one or more batches of enzyme produced using the same manufacturing method.

In some embodiments, the method further comprises a step of assessing lot-to-lot charge variability. In some embodiments, the method of assessing lot-to-lot charge variability comprises comparing graphs trending the relative peak area versus peak groups for each lot of recombinant lysosomal enzyme protein produced during a manufacturing batch.

In some embodiments, the method further comprises a step of assessing batch-to-batch charge variability. In some embodiments, the method of assessing batch-to-batch charge variability comprises comparing graphs trending the relative peak area versus peak groups for each recombinant lysosomal enzyme protein produce by different batches.

In some embodiments, the method further comprises a step of assessing production method charge variability. In some embodiments, the method of assessing production method charge variability comprises comparing graphs trending the relative peak area versus peak groups for each recombinant lysosomal enzyme protein produce by different manufacturing methods.

In some embodiments, capillary zone electrophoresis (CZE) is conducted under conditions such that longer migration times correspond to species of increasing negative charge. In some embodiments, CZE is conducted using a buffer comprising Tris. In some embodiments the buffer system comprises Tris at a concentration ranging from about 20-30 mM. In some embodiments, the buffer system comprises Tris at a concentration of approximately 25 mM. In some embodiments, the buffer system has a pH ranging from approximately 7.5-8.5. In some embodiments, the buffer system has a pH of approximately 8.0.

In some embodiments, capillary zone electrophoresis (CZE) is conducted using a bare fused-silica capillary column. In some embodiments, CZE is conducted using a polyvinyl alcohol (PVA) coated capillary column. In some embodiments, CZE is conducted using a capillary ranging between 50-110 cm in length. In some embodiments, CZE is conducted using a capillary 72 cm in length. In some embodiments, CZE is conducted using a capillary 104 cm in length.

In another aspect, the present invention provides a manufacturing method of analyzing a lysosomal enzyme protein, for example heparan N-sulfatase, comprising characterizing charge profile of an enzyme by capillary zone electrophoresis. In some embodiments, the characterization step comprises a step of separating peak groups corresponding to charge variants by capillary zone electrophoresis.

In some embodiments, the charge profile comprises less than 14 peak groups corresponding to the presence of charge variants. In some embodiments, the charge profile comprises 1, 2, 3, 4, 5, 6, 7, 8, 9, 10, 11, 12, or 13 peak groups corresponding to the presence of charge variants. In some embodiments, the charge profile comprises at least 14 peak groups corresponding to the presence of charge variants. In some embodiments, the charge profile comprises at least 14, 15, 16, 17, 18, 19, 20 or 21 groups corresponding to the presence of charge variants. In some embodiments, the peak groups correspond to the charge variants associated with the absence, presence or varying amount of sialic acid. In some embodiments, the peak groups correspond to the charge variants associated with the absence, presence or varying amount of mannose 6-phosphate (M6P). In some embodiments, the peak groups correspond to the charge variants associated with the absence, presence or varying amount of sialic acid and/or mannose 6-phosphate.

In some embodiments, the characterizing step comprises quantitatively determining relative migration time of each peak group. In some embodiments, the characterizing step comprises quantitatively determining relative peak area for each peak group. In some embodiments, the characterization step comprises quantitatively determining relative migration time and/or relative peak area of each peak group. In some embodiments, the relative migration time of each peak group is determined relative to an electroosmotic flow (EOF) marker. In some embodiments, more than one EOF marker is used. In some embodiments, relative peak area of each peak group is calculated by peak area percentage as compared to the total peak area.

In some embodiments, the manufacturing method further comprises determining the total sialic acid content based on the charge profile. In some embodiments, the manufacturing method further comprises determining the total mannose 6-phosphate content based on the charge profile. In some embodiments, the manufacturing method further comprises determining the total sialic acid and/or mannose 6-phosphate content based on the charge profile. In some embodiments, the manufacturing method of determining the sialic acid content comprises determining the absence, presence or amount of mono-, di- and/or tri-sialylated glycans. In some embodiments, the manufacturing method of determining the M6P content comprises determining the absence, presence or amount of mono- and/or di-M6P.

In some embodiments, the manufacturing method further comprises determining the quality of the lysosomal enzyme protein produced. In some embodiments, enzyme quality is determined at the start of manufacturing production. In some embodiments, enzyme quality is determined at one or more times during production. In some embodiments, enzyme quality is determined during different phases and/or steps of production. In some embodiments, enzyme quality is determined to monitor progression, variation and/or deviations in a production process.

In some embodiments, recombinant lysosomal enzyme protein is produced using a cell culture system. In some embodiments, the cell culture system uses mammalian cells. In some embodiments, the mammalian cells used are human cells. In some embodiments, recombinant lysosomal enzyme is produced at a micro scale production rate. In some embodiments, lysosomal enzyme is produced at a midrange production scale. In some embodiments, lysosomal enzyme is produced at a large scale production rate. In certain specific embodiments, the lysosomal enzyme is HNS.

In some embodiments, the manufacturing method comprises determining if there is variation in the charge profile of a recombinant lysosomal enzyme protein during production. In some embodiments, variation in charge profile is identified by determining a protein charge profile at the start of production. In some embodiments, variation in charge is identified by determining protein charge at one or more times during manufacture. In some embodiments, variation in charge is identified by determining protein charge profile at the end of production. In some embodiments, variation in enzyme charge profile is determined by comparing protein charge profiles collected at one or more times during manufacture. In some embodiments, variation in enzyme charge profile is determined by comparing protein charge profiles collected from one or more batches of enzyme produced using the same manufacturing process. In some embodiments, variation in enzyme charge profile is determined by comparing protein charge profiles collected from one or more lots of enzyme produced within the same manufacturing batch. In some embodiments, variation in enzyme charge profile is determined by comparing protein charge profiles collected from one or more batches of enzyme produced using a different manufacturing process.

In some embodiments, the manufacturing method comprises determining if there is variation in the charge profile of a recombinant lysosomal enzyme protein as compared to a reference. In some embodiments, the reference is a charge profile for an enzyme associated with a lysosomal storage disease. In some embodiments, the references is an average charge profile for one or more different enzymes associated with a lysosomal storage disease. In some embodiments, the reference is an HNS charge profile from an HNS protein produced from a different commercial batch. In some embodiments, the reference is an HNS charge profile from HNS proteins assayed from two or more different lots, within the same commercial batch. In some embodiments, the reference is an HNS charge profile from an FDA approved product. In some embodiments, the reference is an average HNS charge profile generated from an HNS protein assayed from one or more lots and/or batches from the same commercial manufacturing process. In some embodiments, the reference is an average HNS charge profile generated from an HNS protein assayed from one or more lots and/or batches from different commercial manufacturing processes.

In some embodiments, variation in charge profile is identified by determining a HNS charge profile at the start of production. In some embodiments, variation in charge is identified by determining HNS charge at one or more different times during manufacture. In some embodiments, variation in charge is identified by determining HNS charge profile at the end of production. In some embodiments, variation in HNS charge profile is determined by comparing HNS charge profiles collected at one or more times during manufacture. In some embodiments, variation in HNS charge profile is determined by comparing HNS charge profiles collected from one or more batches of HNS enzyme produced using the same manufacturing process. In some embodiments, variation in HNS charge profile is determined by comparing HNS charge profiles collected from one or more lots of HNS enzyme produced within the same manufacturing batch. In some embodiments, variation in HNS charge profile is determined by comparing HNS charge profiles collected from one or more batches of HNS enzyme produced using the same manufacturing process.

In some embodiments, the manufacturing method comprises determining a variation in charge isoform number of a recombinant lysosomal enzyme protein as compared to a reference. In some embodiments, the reference is a charge isoform number obtained by CZE, for an enzyme associated with a lysosomal storage disease. In some embodiments, the reference is an enzyme charge isoform number obtained by CZE, from a different commercial batch. In some embodiments, the reference is an average enzyme charge isoform number obtained by CZE, from two or more different lots, within the same commercial batch. In some embodiments, the reference is an enzyme charge isoform number from an FDA approved product. In some embodiments, the reference is an average enzyme charge isoform number generated from one or more lots and/or batches from the same commercial manufacturing process. In some embodiments, the reference is an average enzyme charge isoform number generated from one or more lots and/or batches from different commercial manufacturing processes.

In some embodiments, variation in charge isoform number is identified by determining an enzyme charge profile at the start of production. In some embodiments, variation in charge is identified by determining an enzyme charge isoform number at one or more times during manufacture. In some embodiments, variation in charge is identified by determining an enzyme charge isoform number at the end of production. In some embodiments, variation in HNS charge profile is determined by comparing an enzyme charge isoform numbers collected at one or more times during manufacture. In some embodiments, variation in an enzyme charge profile is determined by comparing enzyme charge isoform numbers collected from one or more batches of enzyme produced using the same manufacturing process. In some embodiments, variation in an enzyme charge isoform number is determined by comparing enzyme charge profiles collected from one or more lots of enzyme produced within the same manufacturing batch. In some embodiments, variation in enzyme charge isoform number is determined by comparing enzyme charge profiles collected from one or more batches of enzyme produced using the same manufacturing process.

In some embodiments, the manufacturing method further comprises a step of assessing lot-to-lot charge variability. In some embodiments, the method of assessing lot-to-lot charge variability comprises comparing graphs trending the relative peak area versus peak groups for each lot of lysosomal enzyme protein produced during a manufacturing batch.

In some embodiments, the manufacturing method further comprises a step of assessing batch-to-batch charge variability. In some embodiments, the method of assessing batch-to-batch charge variability comprises comparing graphs trending the relative peak area versus peak groups for each lysosomal enzyme protein produce by different batches.

In some embodiments, the manufacturing method further comprises a step of assessing production method charge variability. In some embodiments, the method of assessing production method charge variability comprises comparing graphs trending the relative peak area versus peak groups for each lysosomal enzyme protein produce by different manufacturing processes.

In some embodiments, capillary zone electrophoresis (CZE) is conducted under conditions such that longer migration times correspond to species of increasing negative charges. In some embodiments, CZE is conducted using a buffer comprising Tris. In some embodiments the buffer system comprises Tris at a concentration ranging from about 20-30 mM. In some embodiments, the buffer system comprises Tris at a concentration of approximately 25 mM. In some embodiments, the buffer system has a pH ranging from approximately 7.5-8.5. In some embodiments, the buffer system has a pH of approximately 8.0.

In some embodiments, capillary zone electrophoresis (CZE) is conducted using a bare fused-silica capillary column. In some embodiments, CZE is conducted using a polyvinyl alcohol (PVA) coated capillary column. In some embodiments, CZE is conducted using a capillary ranging between 50-110 cm in length. In some embodiments, CZE is conducted using a capillary ranging between 72 of 104 cm in length.

In some embodiments, the manufacturing method further comprises a step of adjusting a manufacturing condition based on the analysis of the charge profile. In some embodiments the analyzing step is conducted prior to purification. In some embodiments, the analyzing step is conducted during purification. In some embodiments, the analyzing step is conducted one or more times during the manufacturing process. In some embodiments, the analyzing step is conducted before releasing a lot for commercial sale.

In another aspect, the present invention provides a pharmaceutical composition comprising substantially pure lysosomal enzyme protein characterized with a charge profile comprising at least 14 peak groups corresponding to charge variants of the lysosomal enzyme protein, as determined by capillary zone electrophoresis.

In another aspect, the present invention provides a pharmaceutical composition comprising substantially pure heparan N-sulfatase (HNS) protein characterized with a charge profile comprising at least 14 peak groups corresponding to charge variants of the HNS protein, as determined by capillary zone electrophoresis.

In some embodiments, the peak groups correspond to the charge variants associated with the absence, presence or varying amount of sialic acid. In some embodiments, the peak groups correspond to the charge variants associated with the absence, presence or varying amount of mannose 6-phosphate (M6P). In some embodiments, the peak groups correspond to the charge variants associated with the absence, presence or varying amount of sialic acid and/or mannose 6-phosphate.

In some embodiments, the charge variants are selected from the group consisting of mono-, di-, or tri-sialylated glycans. In some embodiments, the charge variants are selected from the group consisting of mono- or di-M6P groups. In some embodiments, the charge variants are selected from the group consisting of mono-sialylated, di-sialylated, tri-sialylated, mono-M6P, di-M6P groups, and combinations thereof.

In some embodiments, the peak group corresponding to mono-M6P has a relative peak area of approximately 8-12% of the total peak areas. In some embodiments, the peak group corresponding to di-M6P has a relative peak area of approximately 10-15% of the total peak areas.

In some embodiments, the recombinant lysosomal protein is one or more lysosomal enzymes listed within Table 2. In some embodiments, the lysosomal enzyme may be a naturally occurring lysosomal enzyme. In some embodiments, a suitable lysosomal enzyme may be a recombinant version of a naturally occurring lysosomal enzyme.

In some embodiments, a lysosomal enzyme suitable for the invention, such as, but not limited to those found in Table 2, may have a wild-type or naturally occurring sequence. In some embodiments, a lysosomal enzyme suitable for the invention may have a modified sequence having substantial homology or identify to the wild-type or naturally-occurring sequence (e.g., having at least 50%, 55%, 60%, 65%, 70%, 75%, 80%, 85%, 90%, 95%, 98% sequence identity to the wild-type or naturally-occurring sequence).

In some embodiments, the recombinant HNS protein has a nucleic acid is encoded by a nucleic acid sequence comprising SEQ ID NO:1. In some embodiments, the nucleic acid sequence encoding HNS is at least 70% identical with SEQ ID NO:1. In some embodiments, the nucleic acid sequence encoding HNS comprises at least 80% homology with SEQ ID NO:1. In some embodiments, recombinant HNS protein has an amino acid sequence comprising SEQ ID NO:2. In some embodiments, recombinant HNS protein has an amino acid sequence at least 70% identical to SEQ ID NO:2. In some embodiments, HNS protein has an amino acid sequence identical to SEQ ID NO:2.

In some embodiments, recombinant HNS protein is produced using a cell culture system. In some embodiments, the cell culture system uses mammalian cells. In some embodiments, the mammalian cells used are human cells. In some embodiments, recombinant HNS is produced at a micro scale production rate. In some embodiments, HNS is produced at a midrange production scale.

In some embodiments, capillary zone electrophoresis (CZE) is conducted under conditions such that longer migration times correspond to species of increasing negative charges. In some embodiments, CZE is conducted using a buffer comprising Tris. In some embodiments the buffer system comprises Tris at a concentration ranging from about 20-30 mM. In some embodiments, the buffer system comprises Tris at a concentration of approximately 25 mM. In some embodiments, the buffer system has a pH ranging from approximately 7.5-8.5. In some embodiments, the buffer system has a pH of approximately 8.0.

In some embodiments, capillary zone electrophoresis (CZE) is conducted using a bare fused-silica capillary column. In some embodiments, CZE is conducted using a polyvinyl alcohol (PVA) coated capillary column. In some embodiments, CZE is conducted using a capillary ranging between 50-110 cm in length. In some embodiments, CZE is conducted using a capillary ranging between 72 of 104 cm in length.

In yet another aspect, the present invention provides a method of treating Sanfilippo A syndrome comprising a step of administering to a subject in need of treatment a pharmaceutical composition comprising substantially pure heparan N-sulfatase (HNS) protein characterized with a charge profile comprising at least 14 peak groups corresponding to charge variants of the HNS protein, as determined by capillary zone electrophoresis.

In some embodiments, the peak groups correspond to the charge variants associated with the absence, presence or varying amount of sialic acid. In some embodiments, the peak groups correspond to the charge variants associated with the absence, presence or varying amount of mannose 6-phosphate (M6P). In some embodiments, the peak groups correspond to the charge variants associated with the absence, presence or varying amount of sialic acid and/or mannose 6-phosphate.

In some embodiments, the charge variants are selected from the group consisting of mono-, di-, or tri-sialylated glycans. In some embodiments, the charge variants are selected from the group consisting of mono- or di-M6P groups. In some embodiments, the charge variants are selected from the group consisting of mono-sialylated, di-sialylated, tri-sialylated, mono-M6P, di-M6P groups, and combinations thereof.

In some embodiments, the peak group corresponding to mono-M6P has a relative peak area of approximately 8-12% of the total peak areas. In some embodiments, the peak group corresponding to di-M6P has a relative peak area of approximately 10-15% of the total peak areas.

In some embodiments, the recombinant lysosomal protein is one or more lysosomal enzymes listed within Table 2. In some embodiments, the lysosomal enzyme may be a naturally occurring lysosomal enzyme. In some embodiments, a suitable lysosomal enzyme may be a recombinant version of a naturally occurring lysosomal enzyme.

In some embodiments, a lysosomal enzyme suitable for the invention, such as, but not limited to those found in Table 2, may have a wild-type or naturally occurring sequence. In some embodiments, a lysosomal enzyme suitable for the invention may have a modified sequence having substantial homology or identify to the wild-type or naturally-occurring sequence (e.g., having at least 50%, 55%, 60%, 65%, 70%, 75%, 80%, 85%, 90%, 95%, 98% sequence identity to the wild-type or naturally-occurring sequence).

In some embodiments, the lysosomal enzyme is HNS. In some embodiments, the HNS is recombinantly produced. In some embodiments, the recombinant HNS protein has a nucleic acid is encoded by a nucleic acid sequence comprising SEQ ID NO:1. In some embodiments, the nucleic acid sequence encoding HNS is at least 70% identical with SEQ ID NO:1. In some embodiments, the nucleic acid sequence encoding HNS comprises at least 80% homology with SEQ ID NO:1. In some embodiments, recombinant HNS protein has an amino acid sequence comprising SEQ ID NO:2. In some embodiments, recombinant HNS protein has an amino acid sequence at least 70% identical to SEQ ID NO:2. In some embodiments, HNS protein has an amino acid sequence identical to SEQ ID NO:2.

In some embodiments, recombinant HNS protein is produced using a cell culture system. In some embodiments, the cell culture system uses mammalian cells. In some embodiments, the mammalian cells used are human cells. In some embodiments, recombinant HNS is produced at a micro scale production rate. In some embodiments, HNS is produced at a midrange production scale.

In some embodiments, capillary zone electrophoresis (CZE) is conducted under conditions such that longer migration times correspond to species of increasing negative charges. In some embodiments, CZE is conducted using a buffer comprising Tris. In some embodiments the buffer system comprises Tris at a concentration ranging from about 20-30 mM. In some embodiments, the buffer system comprises Tris at a concentration of approximately 25 mM. In some embodiments, the buffer system has a pH ranging from approximately 7.5-8.5. In some embodiments, the buffer system has a pH of approximately 8.0.

In some embodiments, capillary zone electrophoresis (CZE) is conducted using a bare fused-silica capillary column. In some embodiments, CZE is conducted using a polyvinyl alcohol (PVA) coated capillary column. In some embodiments, CZE is conducted using a capillary ranging between 50-110 cm in length. In some embodiments, CZE is conducted using a capillary ranging between 72 of 104 cm in length.

BRIEF DESCRIPTION OF THE DRAWINGS

The Figures described below, that together make up the Drawing, are for illustration purposes only, not for limitation.

FIG. 4A-D. demonstrates the effect of buffer pH on peak separation during capillary zone electrophoresis. The charge profile for recombinant HNS was analyzed by capillary zone electrophoresis using Tris buffer at (4A) pH 8.5; (4B) pH 8.0; (4C) pH 7.5 and (4D) pH 7.0.

FIG. 15A-15D. depicts the (15A) native charge profile for recombinant HNS enzyme, along with the charge profile for recombinant HNS pre-treated with either (15B) phosphatase and neuraminidase; (15C) phosphatase; and (15D) neuraminidase for analysis by capillary zone electrophoresis.

DEFINITIONS

Figure 1:
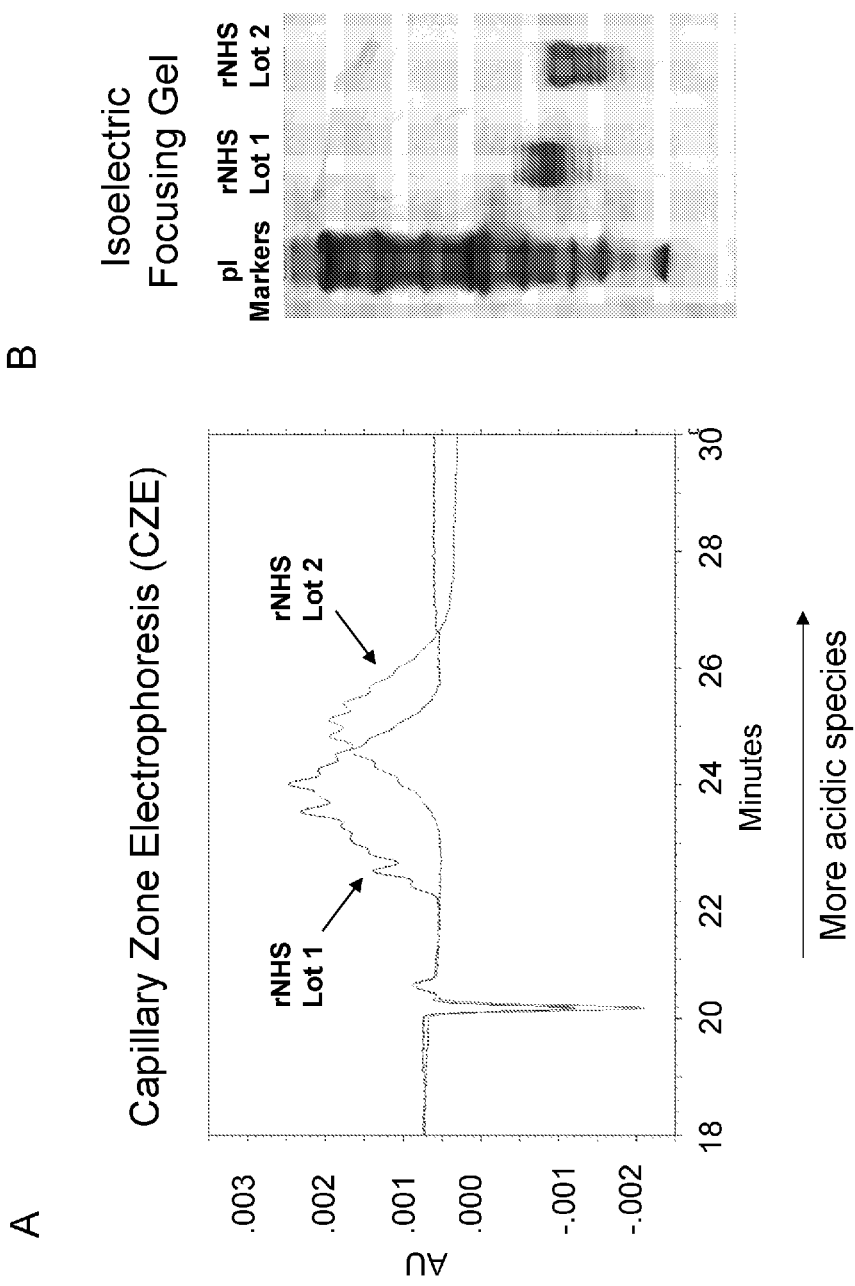
FIGS. 1 A&B. demonstrates the characterization of two different lots of recombinant HNS enzyme (rHNS) produced using the same manufacturing process. The charge profile for two manufacturing lots (rHNS lot 1 and rHNS lot 2) was assayed using capillary zone electrophoresis (A) and an iso-electric focusing gel. Longer migration times correspond to isoforms of increased negative charge.

In order for the present invention to be more readily understood, certain terms are first defined. Additional definitions for the following terms and other terms are set forth throughout the specification.

Amino acid: As used herein, term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc. In some embodiments, amino acids of the present invention may be provided in or used to supplement medium for cell cultures. In some embodiments, amino acids provided in or used to supplement cell culture medium may be provided as salts or in hydrate form.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Batch: As used herein, the term "batch" refers to a completed manufacturing run, in which a product, finished good or component is produced. In some embodiments, a batch comprises multiple "lots". As used herein, the term "lot" refers to a part or fraction of the total completed product produced during the manufacture of a commercial batch. In some embodiments, a batch consists of a single lot. In some embodiments, a batch consists of a plurality of lots. In some embodiments, a batch is partitioned into individual lots based on sample size, FDA requirements and/or shipping conditions. In some embodiments, a batch is partitioned into lots based on specific factions produced during manufacture of the batch.

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. Biological activity can also be determined by in vitro assays (for example, in vitro enzymatic assays such as sulfate release assays). In particular embodiments, where a protein or polypeptide is biologically active, a portion of that protein or polypeptide that shares at least one biological activity of the protein or polypeptide is typically referred to as a "biologically active" portion. In some embodiments, a protein is produced and/or purified from a cell culture system, which displays biologically activity when administered to a subject. In some embodiments, a protein requires further processing in order to become biologically active. In some embodiments, a protein requires posttranslational modification such as, but is not limited to, glycosylation (e.g., sialyation), farnysylation, cleavage, folding, formylglycine conversion and combinations thereof, in order to become biologically active. In some embodiments, a protein produced as a proform (i.e. immature form), may require additional modification to become biologically active.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control. In some embodiments, the control may be a "reference control", which is a sample used for comparison with a test sample, to look for differences or for the purposes of characterization.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodstream. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Gene: The term "gene" as used herein refers to any nucleotide sequence, DNA or RNA, at least some portion of which encodes a discrete final product, typically, but not limited to, a polypeptide, which functions in some aspect of a cellular process. The term is not meant to refer only to the coding sequence that encodes the polypeptide or other discrete final product, but may also encompass regions preceding and following the coding sequence that modulate the basal level of expression, as well as intervening sequences ("introns") between individual coding segments ("exons"). In some embodiments, a gene may include regulatory sequences (e.g., promoters, enhancers, polyadenylation sequences, termination sequences, Kozak sequences, TATA box, etc.) and/or modification sequences. In some embodiments, a gene may include references to nucleic acids that do not encode proteins but rather encode functional RNA molecules such as tRNAs, RNAi-inducing agents, etc.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Various other sequence alignment programs are available and can be used to determine sequence identity such as, for example, Clustal.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease as the individual being treated, who is about the same age as the individual being treated (to ensure that the stages of the disease in the treated individual and the control individual(s) are comparable).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.)

Nucleic acid: As used herein, the term "nucleic acid," in its broadest sense, refers to a compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. In some embodiments, a protein can sometimes include more than one polypeptide chain, for example linked by one or more disulfide bonds or associated by other means. In some embodiments, polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Recombinant protein and Recombinant polypeptide: These terms as used herein refer to a polypeptide expressed from a host cell, that has been genetically engineered to express that polypeptide. In some embodiments, a recombinant protein may be expressed in a host cell derived from an animal. In some embodiments, a recombinant protein may be expressed in a host cell derived from an insect. In some embodiments, a recombinant protein may be expressed in a host cell derived from a yeast. In some embodiments, a recombinant protein may be expressed in a host cell derived from a prokaryote. In some embodiments, a recombinant protein may be expressed in a host cell derived from an mammal. In some embodiments, a recombinant protein may be expressed in a host cell derived from a human. In some embodiments, the recombinantly expressed polypeptide may be identical or similar to a polypeptide that is normally expressed in the host cell. In some embodiments, the recombinantly expressed polypeptide may be foreign to the host cell, i.e. heterologous to peptides normally expressed in the host cell. Alternatively, in some embodiments the recombinantly expressed polypeptide can be a chimeric, in that portions of the polypeptide contain amino acid sequences that are identical or similar to polypeptides normally expressed in the host cell, while other portions are foreign to the host cell.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some embodiments, a replacement enzyme is capable of reducing accumulated materials in mammalian lysosomes or that can rescue or ameliorate one or more lysosomal storage disease symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Subject: As used herein, the term "subject" means any mammal, including humans. In certain embodiments of the present invention the subject is an adult, an adolescent or an infant. Also contemplated by the present invention are the administration of the pharmaceutical compositions and/or performance of the methods of treatment in-utero.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. In some embodiments, the phrase "substantially pure" of "substantially purified", refers to a protein (native or recombinant) which is substantially free of contaminating endogenous materials, such as, e.g., other proteins, lipids, carbohydrates, nucleic acids and other biological materials with which it is naturally associated. For example, a substantially pure molecule can be at least about 60%, by dry weight, preferably about 70%, 80%, 90%, 95% or 99% of the molecule of interest.

Treatment: As used herein, the term "treatment" (also "treat" or "treating") refers to any administration of a therapeutic protein (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., Sanfilippo syndrome). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION OF THE INVENTION

The present invention provides, among other things, improved methods and compositions for the production of recombinant lysosomal enzymes (i.e., heparan N-sulfatase protein) that allows more effective enzyme replacement therapy for treating lysosomal storage disease. In some specific embodiments, the lysosomal enzyme is heparin N-sulfatase and the methods and compositions allow for more effective treatment of Sanfilippo syndrome type A. The present invention encompasses the discovery that capillary zone electrophoresis may be used to accurately characterize recombinant enzymes (i.e. heparan N-sulfatase) during commercial production, by determining their charge and/or glycan profile. Lysosmal enzyme characterization according to the present invention allows for standardization of recombinant protein heterogeneity and optimization of commercial production. Since many features of enzyme composition can adversely affect enzyme activity, the present invention allows more efficient large scale production of biologically active recombinant lysosomal enzyme protein. Various inventive methods and compositions described herein are applicable to other lysosomal enzymes.

Various aspects of the invention are described in further detail in the following subsections. The use of subsections is not meant to limit the invention. Each subsection may apply to any aspect of the invention. In this application, the use of "or" means "and/or" unless stated otherwise.

Lysosomal Enzymes

The present invention may be used profile and/or characterize any enzyme associated with a lysosomal storage disease. In particular, the present invention may be used to characterize a recombinatnely produced lysosomal enzyme during commercial manufacture. According to the present invention, a lysosomal enzyme is contemplated to encompass any enzyme or protein, when targeted to the lysosome, is suitable for the treatment of a lysosomal storage disease. As a non-limiting example, a particularly suitable lysosomal enzyme is a Heparan N-Sulfatase (HNS) protein, which is deficient in Sanfilippo Syndrome Type A disease. Additional exemplary lysosomal enzymes are shown in Table 2.

Heparan N-Sulfatase (HNS)

As used herein, an HNS protein is any protein or portion of a protein that can substitute for at least partial activity of naturally-occurring Heparan N-sulfatase (N-sulphoglucosamine sulphohydrolase) protein or rescue one or more pheontypes or symptoms associated with HNS deficiency and Sanphillipo Syndrome type A. As used herein, the terms "an HNS enzyme" and "an HNS protein", and grammatical equivalents, are used interchangeably.

Typically, the human HNS protein is produced as a precursor form. The precursor form of human HNS contains a signal peptide (amino acid residues 1-20 of the full length precursor) and a chain (amino acid residues 21-502 of the full length precursor) Typically, the precursor form is also referred to as full-length precursor or full-length HNS protein, which contains 502 amino acids. The amino acid sequences of the mature form (SEQ ID NO:2) having the signal peptide removed and full-length precursor (SEQ ID NO:3) of a typical wild-type or naturally-occurring human HNS protein are shown in Table 1. The signal peptide is underlined.

TABLE 1

Human Heparan N-Sulfatase
(N-sulphoglucosamine sulphohydrolase)

| | |
|---|---|
| Mature Form | RPRNALLLLADDGGFESGAYNNSAIATPHLD ALARRSLLFRNAFTSVSSCSPSRASLLTGLP QHQNGMYGLHQDVHHFNSFDKVRSLPLLLSQ AGVRTGIIGKKHVGPETVYPFDFAYTEENGS VLQVGRNITRIKLLVRKFLQTQDDRPPFFLYV AFHDPHRCGHSQPQYGTFCEKFGNGESGMGR IPDWTPQAYDPLDVLVPYFVPNTPAARADLA AQYTTVGRMDQGVGLVLQELRDAGVLNDTLV IFTSDNGIPFPSGRTNLYWPGTAEPLLVSSP EHPKRWGQVSEAYVSLLDLTPTILDWFSIPY PSYAIFGSKTIHLTGRSLLPALEAEPLWATV FGSQSHHEVTMSYPMRSVQHRHFRLVHNLNF KMPFPIDQDFYVSPTFQDLLNRTTAGQPTGW YKDLRHYYYRARWELYDRSRDPHETQNLATD PRFAQLLEMLRDQLAKWQWETHDPWVCAPDG VLEEKLSPQCQPLHNEL (SEQ ID NO: 1) |
| Full-Length Precursor | <u>MSCPVPACCALLLVLGLCRAR</u>PRNALLLLAD DGGFESGAYNNSAIATPHLDALARRSLLFRN AFTSVSSCSPSRASLLTGLPQHQNGMYGLHQ DVHHFNSFDKVRSLPLLLSQAGVRTGIIGKK HVGPETVYPFDFAYTEENGSVLQVGRNITRI KLLVRKFLQTQDDRPPFFLYVAFHDPHRCGHS QPQYGTFCEKFGNGESGMGRIPDWTPQAYDP LDVLVPYFVPNTPAARADLAAQYTTVGRMDQ GVGLVLQELRDAGVLNDTLVIFTSDNGIPFP SGRTNLYWPGTAEPLLVSSPEHPKRWGQVSE AYVSLLDLTPTILDWFSIPYPSYAIFGSKTI HLTGRSLLPALEAEPLWATVFGSQSHHEVTM SYPMRSVQHRHFRLVHNLNFKMPFPIDQDFY VSPTFQDLLNRTTAGQPTGWYKDLRHYYYRA RWELYDRSRDPHETQNLATDPRFAQLLEMLR DQLAKWQWETHDPWVCAPDGVLEEKLSPQCQ PLHNEL (SEQ ID NO: 2) |

In some embodiments, an HNS enzyme is a mature human HNS protein (SEQ ID NO:1). As disclosed herein, SEQ ID NO:1 represents the canonical amino acid sequence for the human HNS protein. In some embodiments, the HNS protein may be a splice isoform and/or variant of SEQ ID NO:1, resulting from transcription at an alternative start site within the 5' UTR of the HNS gene. In some embodiments, a suitable replacement enzyme may be a homologue or an analogue of mature human HNS protein. For example, a homologue or an analogue of mature human HNS protein may be a modified mature human HNS protein containing one or more amino acid substitutions, deletions, and/or insertions as compared to a wild-type or naturally-occurring HNS protein (e.g., SEQ ID NO:1), while retaining substantial HNS protein activity. Thus, in some embodiments, a replacement enzyme suitable for the present invention is substantially homologous to mature human HNS protein (SEQ ID NO:1). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a replacement enzyme suitable for the present invention is substantially identical to mature human HNS protein (SEQ ID NO:1). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a replacement enzyme suitable for the present invention contains a fragment or a portion of mature human HNS protein.

Alternatively, an HNS enzyme is full-length HNS protein. In some embodiments, an HNS enzyme may be a homologue or an analogue of full-length human HNS protein. For example, a homologue or an analogue of full-length human HNS protein may be a modified full-length human HNS protein containing one or more amino acid substitutions, deletions, and/or insertions as compared to a wild-type or naturally-occurring full-length HNS protein (e.g., SEQ ID NO:2), while retaining substantial HNS protein activity. Thus, In some embodiments, an HNS enzyme is substantially homologous to full-length human HNS protein (SEQ ID NO:2). In some embodiments, an HNS enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, an HNS enzyme suitable for the present invention is substantially identical to SEQ ID NO:2. In some embodiments, an HNS enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, an HNS enzyme suitable for the present invention contains a fragment or a portion of full-length human HNS protein. As used herein, a full-length HNS protein typically contains signal peptide sequence.

Homologues or analogues of human HNS proteins can be prepared according to methods for altering polypeptide sequence known to one of ordinary skill in the art such as are found in references that compile such methods. In some embodiments, conservative substitutions of amino acids include substitutions made among amino acids within the following groups: (a) M, I, L, V; (b) F, Y, W; (c) K, R, H; (d) A, G; (e) S, T; (f) Q, N; and (g) E, D. In some embodiments, a "conservative amino acid substitution" refers to an amino acid substitution that does not alter the relative charge or size characteristics of the protein in which the amino acid substitution is made.

In some embodiments, HNS enzymes contain a moiety that binds to a receptor on the surface of cells to facilitate cellular uptake and/or lysosomal targeting. For example, such a receptor may be the cation-independent mannose-6-phosphate receptor (CI-MPR) which binds the mannose-6-phosphate (M6P) residues. In addition, the CI-MPR also binds other proteins including IGF-II. A suitable lysosomal targeting moiety can be IGF-I, IGF-II, RAP, p97, and variants, homologues or fragments thereof (e.g., including those peptide having a sequence at least 70%, 75%, 80%, 85%, 90%, or 95% identical to a wild-type mature human IGF-I, IGF-II, RAP, p97 peptide sequence). In some embodiments, a suitable receptor that the M6P residues bind may be cation-dependent.

Additional Lysosomal Enzymes

As used herein, a lysosomal enzyme is understood to comprise any protein or portion of a protein that can substitute for at least partial activity of a naturally-occurring protein or rescue one or more pheontypes or symptoms associated with a lysosomal storage disease. As used herein, the terms "lysosomal enzyme protein" "Lysosomal protein" and "lysosomal enzyme", are equivalents, and can be used interchangeably.

The present invention may be used to characterize any lysosomal enzymes that can be used to treat any lysosomal storage disease, in particular those lysosomal storage diseases having CNS etiology and/or symptoms, including, but are not limited to, aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, globoid cell leukodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, .beta.-mannosidosis, metachromatic leukodystrophy, mucolipidosis type I, sialidosis types I/II, mucolipidosis types II/III, I-cell disease, mucolipidosis type IIIC pseudo-Hurler polydystrophy, mucopolysaccharidosis type I, mucopolysaccharidosis type II, mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, CLN2 Batten disease, Niemann-Pick disease types A/B, Niemann-Pick disease type C1, Niemann-Pick disease type C2, pycnodysostosis, Schindler disease types I/II, Gaucher disease and sialic acid storage disease.

A detailed review of the genetic etiology, clinical manifestations, and molecular biology of the lysosomal storage diseases are detailed in Scriver et al., eds., The Metabolic and Molecular Basis of Inherited Disease, 7.sup.th Ed., Vol. II, McGraw Hill, (1995). Thus, the enzymes deficient in the above diseases are known to those of skill in the art, some of these are exemplified in Table 2 below:

TABLE 2

Enzymes Associated With Lysosomal Storage Disease

| Disease Name | Enzyme Deficiency | Substance Stored |
| --- | --- | --- |
| Pompe Disease | Acid-α1, 4-Glucosidase | Glycogen α-1-4 linked Oligosaccharides |
| GM1 Gangliodsidosis | β-Galactosidase | $GM_1$ Gangliosides |
| Tay-Sachs Disease | β-Hexosaminidase A | $GM_2$ Ganglioside |

TABLE 2-continued

Enzymes Associated With Lysosomal Storage Disease

| Disease Name | Enzyme Deficiency | Substance Stored |
| --- | --- | --- |
| GM2 Gangliosidosis: AB Variant | $GM_2$ Activator Protein | $GM_2$ Ganglioside |
| Sandhoff Disease | β-Hexosaminidase A&B | $GM_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann Pick, Types A & B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetylglucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| α-Mannosidosis | α-Mannosidase | Mannose/Oligosaccharides |
| β-Mannosidosis | β-Mannosidase | Mannose/Oligosaccharides |
| Fucosidosis | α-L-Fucosidase | Fucosyl/Oligosaccharides |
| Aspartylglucosaminuria | N-Aspartyl-β-Glucosaminidase | Aspartylglucosamine Asparagines |
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

In some embodiments, a suitable lysosomal enzyme may be a naturally occurring lysosomal enzyme. In some embodiments, a suitable lysosomal enzyme may be a recombinant version of a naturally occurring lysosomal enzyme.

In some embodiments, a lysosomal enzyme suitable for the invention may have a wild-type or naturally occurring sequence. In some embodiments, a lysosomal enzyme suitable for the invention may have a modified sequence having substantial homology or identify to the wild-type or naturally-occurring sequence (e.g., having at least 50%, 55%, 60%, 65%, 70%, 75%, 80%, 85%, 90%, 95%, 98% sequence identity to the wild-type or naturally-occurring sequence).

Production of Recombinant Human HNS

The present invention recognizes the need for the high-level, commercial production of biologically active HNS through various manufacturing methods. Because a large number of production factors can influence post-translational modification, and HNS's subsequence biological activity in vivo, methods for characterizing and producing characterized HNS proteins by CZE, are disclosed in the present specification.

In certain aspects, the invention may be used to characterize recombinant HNS protein produced by various means. For example, an HNS protein may be recombinantly produced by utilizing a host cell system engineered to express an HNS-encoding nucleic acid. Nucleic acid molecules disclosed in the present specification are directed toward a wide range of prokaryotic and eukaryotic cells and/or cell lines including, without limitation, cell lines derived from bacteria strains, yeast strains, insect cells, animal cells, mammalian cells and human cells. Alternatively, an HNS protein may be produced by activated an endogenous HNS gene.

Nucleic Acids Encoding HNS

In some embodiments, nucleic acid molecules are provided comprising nucleic acid sequences encoding for a recombinant gene of interest (herein referred to as a transgene) such as an HNS protein described in various embodiments herein. In some embodiments, the nucleic acid encoding a transgene may be modified to provide increased expression of the encoded HNS protein, which is also referred to as codon optimization. For example, the nucleic acid encoding a transgene can be modified by altering the open reading frame for the coding sequence. As used herein, the term "open reading frame" is synonymous with "ORF" and means any nucleotide sequence that is potentially able to encode a protein, or a portion of a protein. An open reading frame usually begins with a start codon (represented as, e.g. AUG for an RNA molecule and ATG in a DNA molecule in the standard code) and is read in codon-triplets until the frame ends with a STOP codon (represented as, e.g. UAA, UGA or UAG for an RNA molecule and TAA, TGA or TAG in a DNA molecule in the standard code). As used herein, the term "codon" means a sequence of three nucleotides in a nucleic acid molecule that specifies a particular amino acid during protein synthesis; also called a triplet or codon-triplet. For example, of the 64 possible codons in the standard genetic code, two codons, GAA and GAG encode the amino acid Glutamine whereas the codons AAA and AAG specify the amino acid Lysine. In the standard genetic code three codons are stop codons, which do not specify an amino acid. As used herein, the term "synonymous codon" means any and all of the codons that code for a single amino acid. Except for Methionine and Tryptophan, amino acids are coded by two to six synonymous codons. For example, in the standard genetic code the four synonymous codons that code for the amino acid Alanine are GCA, GCC, GCG and GCU, the two synonymous codons that specify Glutamine are GAA and GAG and the two synonymous codons that encode Lysine are AAA and AAG.

In some embodiments, a nucleic acid encoding the open reading frame of an HNS protein may be modified using standard codon optimization methods. Various commercial algorithms for codon optimization are available and can be used to practice the present invention. Typically, codon optimization does not alter the encoded amino acid sequences. In some embodiments, codon optimization may lead to amino acids alteration such as substitution, deletion or insertion. Typically, such amino acid alteration does not substantially alter the protein activity. Exemplary nucleic acid sequences encoding an HNS are shown in SEQ ID NO:3.

Exemplary Nucleic Acid Sequence Encoding Heparan N-Sulphatase (HNS)

(SEQ ID NO: 3)
ATGAGCTGCCCCGTGCCCGCCTGCTGCGCGCTGCTGCTAGTCCTGGGG

CTCTGCCGGGCGCGTCCCCGGAACGCACTGCTGCTCCTCGCGGATGAC

GGAGGCTTTGAGAGTGGCGCGTACAACAACAGCGCCATCGCCACCCCG

CACCTGGACGCCTTGGCCCGCCGCAGCCTCCTCTTTCGCAATGCCTTC

ACCTCGGTCAGCAGCTGCTCTCCCAGCCGCGCCAGCCTCCTCACTGGC

CTGCCCCAGCATCAGAATGGGATGTACGGGCTGCACCAGGACGTGCAC

CACTTCAACTCCTTCGACAAGGTGCGGAGCCTGCCGCTGCTGCTCAGC

CAAGCTGGTGTGCGCACAGGCATCATCGGGAAGAAGCACGTGGGGCCG

GAGACCGTGTACCCGTTTGACTTTGCGTACACGGAGGAGAATGGCTCC

GTCCTCCAGGTGGGGCGGAACATCACTAGAATTAAGCTGCTCGTCCGG

AAATTCCTGCAGACTCAGGATGACCGGCCTTTCTTCCTCTACGTCGCC

TTCCACGACCCCCACCGCTGTGGGCACTCCCAGCCCCAGTACGGAACC

TTCTGTGAGAAGTTTGGCAACGGAGAGAGCGGCATGGGTCGTATCCCA

GACTGGACCCCCAGGCCTACGACCCACTGGACGTGCTGGTGCCTTAC

TTCGTCCCCAACACCCCGGCAGCCCGAGCCGACCTGGCCGCTCAGTAC

ACCACCGTCGGCCGCATGGACCAAGGAGTTGGACTGGTGCTCCAGGAG

CTGCGTGACGCCGGTGTCCTGAACGACACACTGGTGATCTTCACGTCC

GACAACGGGATCCCCTTCCCCAGCGGCAGGACCAACCTGTACTGGCCG

GGCACTGCTGAACCCTTACTGGTGTCATCCCCGGAGCACCCAAAACGC

TGGGGCCAAGTCAGCGAGGCCTACGTGAGCCTCCTAGACCTCACGCCC

ACCATCTTGGATTGGTTCTCGATCCCGTACCCCAGCTACGCCATCTTT

GGCTCGAAGACCATCCACCTCACTGGCCGGTCCTCCTGCCGGCGCTG

GAGGCCGAGCCCTCTGGGCCACCGTCTTTGGCAGCCAGAGCCACCAC

GAGGTCACCATGTCCTACCCCATGCGCTCCGTGCAGCACCGGCACTTC

CGCCTCGTGCACAACCTCAACTTCAAGATGCCCTTTCCCATCGACCAG

GACTTCTACGTCTCACCCACCTTCCAGGACCTCCTGAACCGCACCACA

GCTGGTCAGCCCACGGGCTGGTACAAGGACCTCCGTCATTACTACTAC

CGGGCGCGCTGGGAGCTCTACGACCGGAGCCGGGACCCCCACGAGACC

CAGAACCTGGCCACCGACCCGCGCTTTGCTCAGCTTCTGGAGATGCTT

CGGGACCAGCTGGCCAAGTGGCAGTGGGAGACCCACGACCCCTGGGTG

TGCGCCCCGACGCGTCCTGGAGGAGAAGCTCTCTCCCAGTGCCAG

CCCCTCCACAATGAGCTGTGACCATCCCAGGAGGCCTGTGCACACATC

CCAGGCATGTCCCAGACACATCCCACACGTGTCCGTGTGGCCGGCCAG

CCTGGGGAGTAGTGGCAACAGCCCTTCCGTCCACACTCCCATCCAAGG

AGGGTTCTTCCTTCCTGTGGGGTCACTCTTGCCATTGCCTGGAGGGGG

ACCAGAGCATGTGACCAGAGCATGTGCCCAGCCCCTCCACCACCAGGG

GCACTGCCGTCATGGCAGGGGACACAGTTGTCCTTGTGTCTGAACCAT

GTCCCAGCACGGGAATTCTAGACATACGTGGTCTGCGGACAGGGCAGC

```
-continued
GCCCCCAGCCCATGACAAGGGAGTCTTGTTTTCTGGCTTGGTTTGGGG

ACCTGCAAATGGGAGGCCTGAGGCCCTCTTCAGGCTTTGGCAGCCACA

GATACTTCTGAACCCTTCACAGAGAGCAGGCAGGGGCTTCGGTGCCGC

GTGGGCAGTACGCAGGTCCCACCGACACTCACCTGGGAGCACGGCGCC

TGGCTCTTACCAGCGTCTGGCCTAGAGGAAGCCTTTGAGCGACCTTTG

GGCAGGTTTCTGCTTCTTCTGTTTTGCCCCATGGTCAAGTCCCTGTTC

CCCAGGCAGGTTTCAGCTGATTGGCAGCAGGCTCCCTGAGTGATGAGC

TTGAACCTGTGGTGTTTCTGGGCAGAAGCTTATCTTTTTTGAGAGTGT

CCGAAGATGAAGGCATGGCGATGCCCGTCCTCTGGCTTGGGTTAATTC

TTCGGTGACACTGGCATTGCTGGGTGGTGATGCCCGTCCTCTGGCTTG

GGTTAATTCTTCGGTGACACTGGCGTTGCTGGGTGGCAATGCCCATCC

TCTGCCTTGGGTTAATTCTTCGGTGACACTGGCGTTGCTGGGTGGCGA

TGCCCGTCCTCTGGCTTGGGTTAATTCTTGGATGACGTCGGCGTTGCT

GGGAGAATGTGCCGTTCCTGCCCTGCCTCCACCCACCTCGGGAGCAGA

AGCCCGGCCTGGACACCCCTCGGCCTGGACACCCCTCGAAGGAGAGGG

CGCTTCCTTGAGTAGGTGGGCTCCCCTTGCCCTTCCCTCCCTATCACT

CCATACTGGGGTGGGCTGGAGGAGGCCACAGGCCAGCTATTGTAAAAG

CTTTTTATTTTAGTAAAATATACAGAAGTTCTTTTTCTGAAAA
```

In some embodiments, a nucleotide change may alter a synonymous codon within the open reading frame in order to agree with the endogenous codon usage found in a particular heterologous cell selected to express HNS. Alternatively or additionally, a nucleotide change may alter the G+C content within the open reading frame to better match the average G+C content of open reading frames found in endogenous nucleic acid sequence present in the heterologous host cell. A nucleotide change may also alter a polymononucleotide region or an internal regulatory or structural site found within an HNS sequence. Thus, a variety of modified or optimized nucleotide sequences are envisioned including, without limitation, nucleic acid sequences providing increased expression of HNS proteins in a prokaryotic cell; yeast cell; insect cell; and in a mammalian cell.

Thus, in some embodiments, a nucleic acid encoding an HNS protein suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. Typically, a modified nucleic acid encodes an HNS protein with or without amino acid sequence alteration. In the event there is amino acid alteration, such alteration typically does not substantially alter HNS protein activity.

Expression Vectors/Cell Lines

A nucleic acid sequence encoding a lysosomal enzyme protein as described in the present application, can be molecularly cloned (inserted) into a suitable vector for propagation or expression in a host cell. A wide variety of expression vectors can be used to practice the present invention, including, without limitation, a prokaryotic expression vector; a yeast expression vector; an insect expression vector and a mammalian expression vector. Exemplary vectors suitable for the present invention include, but are not limited to, viral based vectors (e.g., AAV based vectors, retrovirus based vectors, plasmid based vectors). Typically, a nucleic acid encoding lysosomal enzyme protein is operably linked to various regulatory sequences or elements.

As used herein, the term "host cells" refers to cells that can be used to produce recombinant lysosomal enzyme. In particular, host cells are suitable for producing recombinant lysosomal enzymes at a large scale. Suitable host cells can be derived from a variety of organisms, including, but not limited to, mammals, plants, birds (e.g., avian systems), insects, yeast, and bacteria. In some embodiments, host cells are mammalian cells. In some embodiments, a suitable host cell is not a endosomal acidification-deficient cell.

Mammalian Cell Lines

Any mammalian cell or cell type susceptible to cell culture, and to expression of polypeptides, may be utilized in accordance with the present invention as a host cell. Non-limiting examples of mammalian cells that may be used in accordance with the present invention include human embryonic kidney 293 cells (HEK293), HeLa cells; BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells +/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; and a human hepatoma line (Hep G2). In some embodiments, a suitable mammalian cell is not a endosomal acidification-deficient cell.

Additionally, any number of commercially and non-commercially available hybridoma cell lines that express polypeptides or proteins may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

Non-Mammalian Cell Lines

Any non-mammalian derived cell or cell type susceptible to cell culture, and to expression of polypeptides, may be utilized in accordance with the present invention as a host cell. Non-limiting examples of non-mammalian host cells and cell lines that may be used in accordance with the present invention include cells and cell lines derived from *Pichia pastoris, Pichia methanolica, Pichia angusta, Schizosaccharomyces pombe, Saccharomyces cerevisiae,* and *Yarrowia lipolytica* for yeast; *Sodoptera frugiperda, Trichoplusis ni, Drosophila melangoster* and *Manduca sexta* for insects; and *Escherichia coli, Salmonella typhimurium, Bacillus subtilis, Bacillus licheniformis, Bacteroides fragilis, Clostridia perfringens, Clostridia difficile* for bacteria; and *Xenopus Laevis* from amphibian.

Adaptable to Adherent Vs Suspension Growth

In certain embodiments, a host cell is selected for generating a cell line based on certain preferable attributes or growth under particular conditions chosen for culturing cells. It will be appreciated by one skilled in the art, such attributes may be ascertained based on known characteristic and/or traits of an established line (i.e. a characterized commercially available cell line) or though empirical evaluation. In some embodiments, a cell line may be selected for its ability to grow on a feeder layer of cells. In some embodiments, a cell line may be selected for its ability to grow in suspension. In some embodiments, a cell line may be selected for its ability to grow as an adherent monolayer of cells. In some embodiments, such cells can be used with any tissue culture vessel or any vessel treated with a suitable adhesion substrate. In some embodiments, a suitable adhesion substrate is selected from the group consisting of collagen (e.g. collagen I, II, II, or IV), gelatin, fibronectin, laminin, vitronectin, fibrinogen, BD Matrigel™, basement membrane matrix, dermatan sulfate proteoglycan, Poly-D-Lysine and/or combinations thereof. In some embodiments, an adherent host cell may be selected and modified under specific growth conditions to grow in suspension. Such methods of modifying an adherent cell to grown in suspension are known in the art. For example, a cell may be conditioned to grow in suspension culture, by gradually removing animal serum from the growth media over time.

Cell Culture System and Methods

Various cell culture medium and conditions may be used to produce a recombinant lysosomal enzyme protein. For example, a recombinant lysosomal enzyme protein may be produced in serum-containing or serum-free medium. In some embodiments, a recombinant HNS protein is produced in serum-free medium. In some embodiments, a recombinant HNS protein is produced in an animal free medium, i.e., a medium that lacks animal-derived components. In some embodiments, a recombinant HNS protein is produced in a chemically defined medium. As used herein, the term "chemically-defined nutrient medium" refers to a medium of which substantially all of the chemical components are known. In some embodiments, a chemically defined nutrient medium is free of animal-derived components such as serum, serum derived proteins (e.g., albumin or fetuin), and other components. In some cases, a chemically-defined medium comprises one or more proteins (e.g., protein growth factors or cytokines.) In some cases, a chemically-defined nutrient medium comprises one or more protein hydrolysates. In other cases, a chemically-defined nutrient medium is a protein-free media, i.e., a serum-free media that contains no proteins, hydrolysates or components of unknown composition.

In some embodiments, a chemically defined medium may be supplemented by one or more animal derived components. Such animal derived components include, but are not limited to, fetal calf serum, horse serum, goat serum, donkey serum, human serum, and serum derived proteins such as albumins (e.g., bovine serum albumin or human serum albumin). While the addition of serum is desirable because it contains constituents, such as vitamins, amino acids, growth factors, and hormones, it also constitutes a concentrated source of exogenous protein which can impede recombinant protein purification. Thus, in some embodiments, a suitable medium is a xeno-free media, e.g., a medium that does not contain any bovine serum or bovine serum derived components. For example, a xeno-free medium may contain one or more of human serum albumin, human transferrin, human insulin, and human lipids. In some embodiments, a suitable medium contains fetuin-depleted serum. Fetuin may be depleted from serum using various methods known in the art. For example, fetuin may be depleted from serum by antibody affinity chromatography. (See, e.g., Toroian D and Price P A, Calcif Tissue Int (2008) 82:116-126). In some embodiments, a suitable medium is fetuin-free.

Various cell culture conditions may be used to produce recombinant lysosomal enzyme proteins at large scale including, but not limited to, roller bottle cultures, bioreactor batch cultures and bioreactor fed-batch cultures. In some embodiments, recombinant lysosomal enzyme protein is produced by cells cultured in suspense. In some embodiments, recombinant lysosomal enzyme protein is produced by adherent cells.

Purification of Expressed Lysosomal Enzyme Protein

Various methods may be used to purify or isolate lysosomal enzyme proteins produced according to various methods described herein. In some embodiments, the expressed enzyme is secreted into the medium and thus cells and other solids may be removed, as by centrifugation or filtering for example, as a first step in the purification process. Alternatively or additionally, the expressed enzyme is bound to the surface of the host cell. In this embodiment, the host cells expressing the polypeptide or protein are lysed for purification. Lysis of mammalian host cells can be achieved by any number of means well known to those of ordinary skill in the art, including physical disruption by glass beads and exposure to high pH conditions.

The lysosomal enzyme protein may be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference). For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the polypeptide or protein during the purification process. Protease inhibitors are particularly desired when cells must be lysed in order to isolate and purify the expressed polypeptide or protein.

Characterization of Purified Lysosomal Enzyme Proteins

A purified lysosomal enzyme protein as described in the present application, can be characterized by assaying for several biological properties. As used herein, the term "biological property" refers to a chemical, physiologic or molecule feature, corresponding to a biological activity and/or function, and may be altered (i.e. enhance, diminish, disrupt and/or perturb) as a result of the addition, deletion and/or modification of the canonical nucleic acid or amino acid sequence. In some embodiments, an lysosomal enzyme protein may be characterized for one or more biological properties to determine its purity in reference to other proteins in a heterogeneous mixture.

In some embodiments, an lysosomal enzyme protein may be characterized for a biological property by comparing the uncharacterized lysosomal enzyme protein to a known characterized reference protein, to determine and/or predict the chemical or physical properties of the uncharacterized lysosomal enzyme protein. In some embodiments, the reference protein, is a commercially available protein standard. In some embodiments, the reference protein is a purified enzyme, which is associated with a lysosomal storage disease. In some embodiments, the reference protein is a purified lysosomal enzyme. In some embodiments, the reference protein is a purified recombinant lysosomal enzyme. In some embodiments, the reference protein is a modified recombinant lysosomal enzyme protein, modified using any of a number of methods known to those in the art, such as but not limited to, those methods described in the current specification.

In some embodiments, the reference protein is a purified HNS protein. In some embodiments, the reference protein is a purified recombinant HNS protein. In some embodiments, the reference protein is a modified recombinant HNS protein, modified using any of a number of methods known to those in the art, such as but not limited to, those methods described in the current specification.

In some embodiments, a lysosomal enzyme protein, such as HNS, may be characterized for a specific biological property to evaluate a potential method of manufacture. In some embodiments, a lysosomal enzyme protein may be characterized to compare one or more of its biological properties to that of another lysosomal enzyme protein produced using the same manufacturing process. In some embodiments, a lysosomal enzyme protein may be characterized to compare one or more of its biological properties to a different lot of lysosomal enzyme protein produced using the same manufacturing process. In some embodiments, a lysosomal enzyme protein may be characterized to compare one or more of its biological properties to a lysosomal enzyme protein produced in a different manufacturing batch. In some embodiments, a lysosomal enzyme protein may be characterized to compare one or more of its biological properties to a lysosomal enzyme protein produced using a different manufacturing process. In some embodiments, a lysosomal enzyme protein may be characterized to compare one or more of its biological properties to one or more lysosomal enzyme proteins produced during various stages of manufacture. In some embodiments, a lysosomal enzyme protein may be characterized to compare one or more of its biological properties to another purified HNS protein (using either the same or different manufacturing methods), for the purpose of altering, modifying, monitoring and/or changing a potential manufacturing process.

In some embodiments, a n HNS pro lysosomal enzyme protein may be characterized for a biological property to predict its ability to carry-out its known and/or predicted biological function in vitro. In some embodiments, a lysosomal enzyme protein may be characterized for a biological property to predict its ability to carry-out its known and/or predicted biological function in vivo. In some embodiments, a lysosomal enzyme protein may be characterized for a biological property to predict a change (increase and/or decrease) in it pharmacological properties, such as, but not limited to, pharmacodynamics, pharmacokinetics, bioavailability, volume distribution, catabolism, steady-state serum level and/or clearance. In some embodiments, a lysosomal enzyme protein may be characterized for a biological property to predict it's cellular uptake in vivo.

Purity and Concentration

In some embodiments, a lysosomal enzyme purity may be characterized according to protein size, shape or concentration. Specifically, purity of purified recombinant HNS may be measured by the level of various impurities (e.g., host cell protein or host cell DNA) present during various stages of manufacture or in the final product. For example, the purity and/or concentration of a lysosomal enzyme protein may be measured by ELISA or SDS-PAGE. In some embodiments, the protein concentration of a recombinant lysosomal enzyme protein may be determined by any suitable method known in the art for determining protein concentrations. In some specific embodiments, the protein concentration is determined by an ultraviolet light absorbance assay. Such absorbance assays are typically conducted at about a 280 nm wavelength ($A_{280}$). Various assay controls may be used, in particular, those acceptable to regulatory agencies such as FDA.

Enzymatic Activity

Purified recombinant lysosomal enzyme protein may also be characterized by evaluating functional and/or biological activity. The enzyme activity of a recombinant lysosomal enzyme composition may be determined using methods known in the art. Typically the methods involve detecting the removal of N-linked sulfate moieties from a synthetic substrate, which is known as sulfate release assay. One example of an enzyme activity assay involves the use of ion chromatography. This method quantifies the amount of sulfate ions that are enzymatically released by a recombinant heparan sulfatase (i.e., HNS) from a substrate. The substrate may be a natural substrate or a synthetic substrate. In some cases, the substrate is heparin sulfate, dermatan sulfate, or a functional equivalent thereof. In some embodiments, biological activity may be determined by measuring the removal of sulfate from a 4-methylumbelliferyl-sulfate (4-MUF-sulfate) substrate to form the fluorescent methylumbelliferone. In this example, the fluorescence signal generated by a test sample can be used to calculate enzyme activity (in mU/mL) using a standard of 4-MUF. One milliunit of activity is defined as the quantity of enzyme required to convert 1 nanomole of 4-MUF-sulfate to 4-MUF in 1 minute at 37° C. Specific activity may then calculated by dividing the enzyme activity by the protein concentration.

Charge Profile

Purified recombinant lysosomal enzyme protein may be characterized by the charge profile associated with the protein. Typically, protein charge profile reflects the pattern of residue side chain charges, typically present on the surface of the protein. As used herein, the term "charge profile" refers to a set of values representing the amount of protein that elutes from a column and/or capillary at a given point, resulting from its native charge at a given pH. The difference in charge associated with a protein, can be influence by several factors, such as, but not limited to, modification of the protein post-translationally. For example, in the case of glycoproteins (such as many human lysosomal enzymes, including HNS), the result in charge variation is believed to be attributed to charged terminal carbohydrate moieties such as sialic acid and mannose-6-phosphate (M6P). Without wishing to be bound by any theory, it is thought that glycan linkage along with the shape and complexity of the branch structure may impact in vivo clearance, lysosomal targeting, bioavailability, and/or efficacy.

Therefore, it should be appreciated that the term "charge profile" can be further characterized into different charge related classifications, such as "charge isoform number" and "glycan map". As used herein, the term "charge isoform number" refers to the number of differently charged versions of a protein present in a heterogeneous sample. For example, in some embodiments, characterization of recombinant human HNS by CZE, using the methods described herein, results in 14 distinct peaks, each corresponding to a different charge isoform.

In some embodiments, a charge profile is determined for a purified lysosomal enzyme protein using capillary zone electrophoresis. In general, purified lysosomal enzyme protein is placed in a capillary tube containing a buffer equilibrated to a specific pH. Application of a strong electromagnetic field results in a bulk flow toward the cathode, with a elution rate that is influenced by several variables, such as pH, buffer composition and buffer strength. This bulk movement of solutes is caused by electroosmotic flow, leading to separation of the sample based on the charge-to-mass ration of each individual analyte. More negatively charged (more acidic) lysosomal enzyme protein (i.e., HNS species) elute earlier than less negatively charged (less acidic) lysosomal enzyme protein (i.e., HNS species).

In some embodiments, the charge profile for a lysosomal enzyme protein is determined by CZE using a buffer selected from the group consisting of Tris, Borate, HEPES, Phosphate, Gly-Gly and/or combinations thereof. In some embodiments, the charge profile of an HNS protein is determined by CZE using a Tris buffer. In some embodiments, the charge profile for an HNS protein is determined by CZE using a buffer with a concentration of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mM. In some embodiments, the charge profile of an HNS protein is determined by CZE using a Tris buffer at a concentration of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 of 100 mM. In some embodiments, the charge profile of an HNS protein is determined by CZE using a Borate buffer at a concentration of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 of 100 mM. In some embodiments, the charge profile of an HNS protein is determined by CZE using a HEPES buffer at a concentration of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 of 100 mM. In some embodiments, the charge profile of an HNS protein is determined by CZE using a Phosphate buffer at a concentration of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 of 100 mM. In some embodiments, the charge profile of an HNS protein is determined by CZE using a Gly-Gly buffer at a concentration of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 of 100 mM. In some embodiments, the charge profile of a lysosomal enzyme protein is determined by CZE using a Tris buffer at a concentration of 25, 50 or 100 mM. In some embodiments, the charge profile of an HNS protein is determined by CZE using a Tris buffer at a concentration of 25 mM.

In some embodiments, the charge profile of a lysosomal enzyme protein is determined by CZE using a buffer equilibrated to a pH of 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 or 9.0. In some embodiments, the charge profile of an HNS protein is determined by CZE using a Tris buffer at a pH of 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 or 9.0. In some embodiments, the charge profile of an HNS protein is determined by CZE using a Borate buffer at a pH of 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 or 9.0. In some embodiments, the charge profile of an HNS protein is determined by CZE using a Phosphate buffer at a pH of 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 or 9.0. In some embodiments, the charge profile of a lysosomal enzyme protein is determined by CZE using a Gly-Gly buffer at a pH of 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 or 9.0. In some embodiments, the charge profile of a lysosomal enzyme protein is determined by CZE using a Tris buffer at a pH between 7.9 and 8.11. In some embodiments, the charge profile of a lysosomal enzyme protein is determined by CZE using a Tris buffer at a pH of 8.0.

In some embodiments, the charge profile of a lysosomal enzyme protein is determined by CZE using a bare-fused silica capillary tube. In some embodiments, the charge profile of a lysosomal enzyme protein is determined by CZE using a polyvinyl alcohol capillary tube. In some embodiments, the charge profile of a lysosomal enzyme protein is determined by CZE using capillary tube 50, 55, 60, 65, 70, 75, 80, 85, 90, 95, 100, 110, 115 or 120 cm in length. In some embodiments, the charge profile of lysosomal enzyme protein is determined by CZE using a capillary tube with a length ranging between 50-110 cm. In some embodiments, the charge profile of a lysosomal enzyme protein is determined by CZE using a capillary tube 72 cm in length. In some embodiments, the charge profile of a lysosomal enzyme protein is determined by CZE using a capillary tube 104 cm in length.

In some embodiments, the charge profile of a lysosomal enzyme protein is determined by CZE using a capillary tube with an i.d. (inner diameter) of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 µm. In some embodiments, the charge profile of a lysosomal enzyme protein is determined by CZE using a capillary tube with an i.d ranging between 25-110 µm.

In some embodiments, the charge profile of a lysosomal enzyme protein is determined by CZE using a voltage of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 kV. In some embodiments, the charge profile of a lysosomal enzyme protein is determined by CZE using a voltage between 15-30 kV. In some embodiments, the charge profile of a lysosomal enzyme protein is determined by CZE using a voltage of 30 kV.

In some embodiments, the charge profile of a lysosomal enzyme protein is determined by CZE using a temperature of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50° C. In some embodiments, the charge profile of a lysosomal enzyme protein is determined by CZE using a temperature of 30° C.

Figure 7:
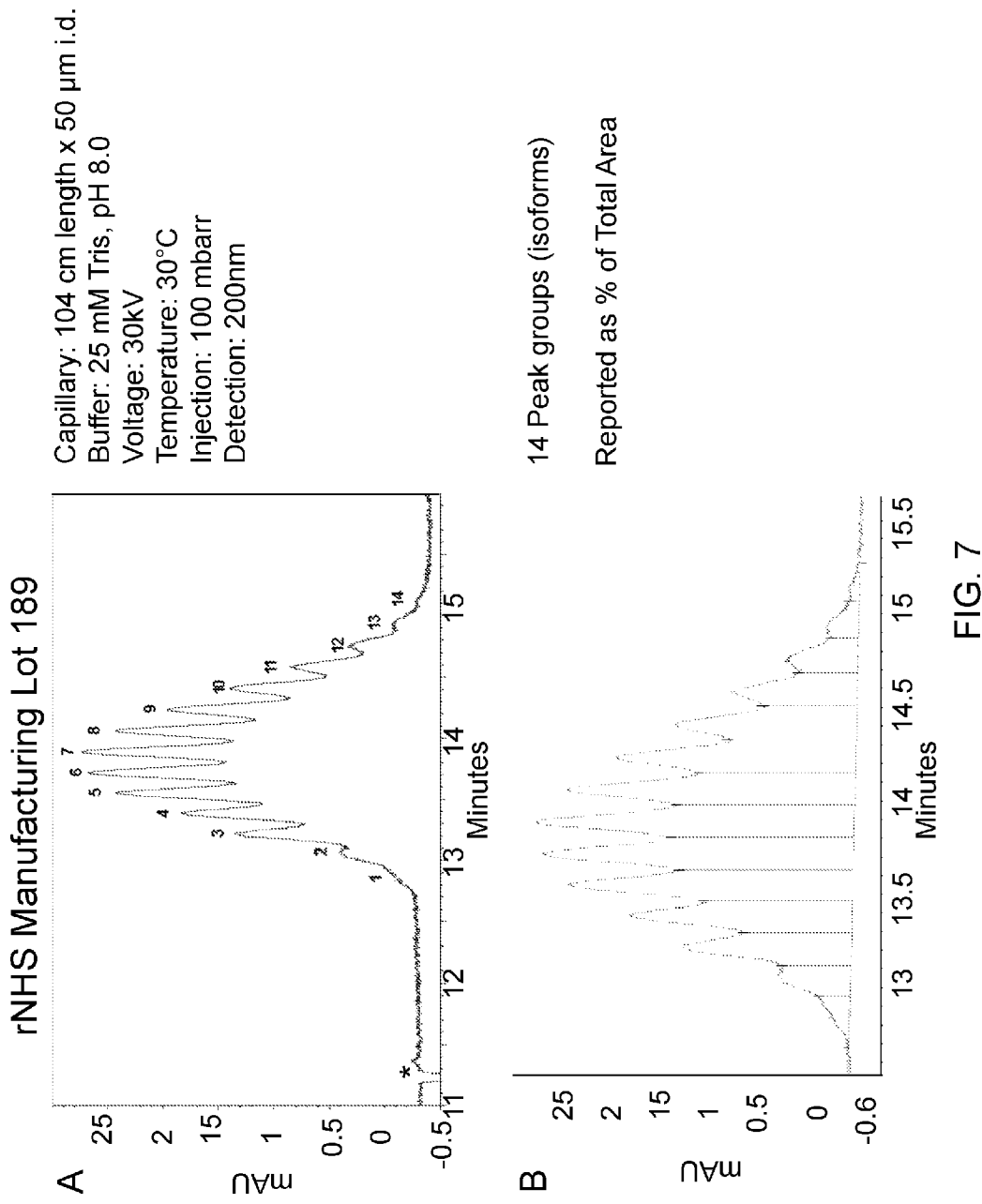
FIGS. 7A&B. demonstrates exemplary capillary zone electrophoresis conditions that allow for the (A) separation and (B) integration of 14 HNS isoforms with different charge profiles.

In some embodiments, a purified lysosomal enzyme protein composition exhibits at least 5, 6, 7, 8, 9, 10, 11, 12, 13, 14, 15, 16, 17, 18, 19 or 20 different charge isoform peaks in its charge profile. In some embodiments, a purified lysosomal enzyme protein composition exhibits at least 14 different charge isoform peaks in its charge profile. An exemplary charge profile of HNS is depicted in the Examples section and in FIG. 7. As shown in FIG. 7, 14 peaks are labeled (1-14) in the order of increasing negative charge and decreasing contribution to total peak area of the chromatogram. In some embodiments, the charge profile for a purified recombinant lysosomal enzyme protein composition contains a different number, size, shape or time interval of peaks depending on the amount of negative or positive charges on the surface of the protein. In some embodiments, a recombinant lysosomal enzyme protein composition has a charge profile that has fewer than 14 (e.g., fewer than 5, 4, 3, or 2) peaks. Typically, a charge profile is considered more homogenous if there are fewer peaks.

Glycan Mapping

In some embodiments, a purified recombinant lysosomal enzyme protein may be characterized by their proteoglycan composition, typically referred to as glycan mapping. As used herein, the term "glycan map" refers to the characteristic map or footprint of a protein produced during chromatographic charge separation, following enzymatic protein cleavage. For example, in some embodiments, recombinant lysosomal enzyme protein may be characterized by CZE following enzymatic cleavage using methods described herein, followed by HPLC chromatography to produce a condensed glycan map.

Various enzymes may be used for enzymatic digestion including, but not limited to, suitable glycosylases, peptidases (e.g., Endopeptidases, Exopeptidases), proteases, and phosphatases. In some embodiments, a suitable enzyme is alkaline phosphatase. In some embodiments, a suitable enzyme is neuraminidase. Glycans (e.g., phosphoglycans) may be detected by chromatographic analysis. For example, phosphoglycans may be detected by High Performance Anion Exchange Chromatography with Pulsed Amperometric Detection (HPAE-PAD) or size exclusion High Performance Liquid Chromatography (HPLC). The quantity of glycan (e.g., phosphoglycan) represented by each peak on a glycan map may be calculated using a standard curve of glycan (e.g., phosphoglycan), according to methods known in the art and disclosed herein.

In some embodiments, a lysosomal enzyme protein, for example HNS, according to the present invention exhibits a glycan map comprising seven peak groups indicative of neutral (peak group 1), mono-sialylated (peak group 2), di-sialylated (peak group 3), monophosphorylated (peak group 4), tri-sialylated (peak group 5), tetra-sialylated (peak group 6), and diphosphorylated (peak group 7), respectively. Exemplary glycan maps of I2S are depicted in FIG. 14B. In some embodiments, a purified recombinant I2S has a glycan map that has fewer than 7 peak groups (e.g., a glycan map with 6, 5, 4, 3, or 2 peaks groups). In some embodiments, a purified recombinant I2S has a glycan map that has more than 7 peak groups (e.g., 8, 9, 10, 11, 12 or more). In some embodiments, the relative amount of glycan corresponding to each peak group may be determined based on the peak group area relative to the corresponding peak group area in a predetermined reference standard. Various reference standards for glycan mapping are known in the art and can be used to practice the present invention.

Pharmaceutical Composition and Administration

Purified recombinant lysosomal enzyme protein may be administered to a patient suffering from a lysosomal storage disease, in accordance with known methods. In some specific examples, purified HNS protein may be administered to a Sanphillipo Syndrome type A patient in accordance with known methods. For example, a purified recombinant lysosomal enzyme protein, such as HNS, may be delivered intravenously, subcutaneously, intramuscularly, parenterally, transdermally, or transmucosally (e.g., orally or nasally)).

In some embodiments, a recombinant lysosomal enzyme protein or a pharmaceutical composition containing the same is administered to a subject by intravenous administration.

In some embodiments, a recombinant lysosomal enzyme protein or a pharmaceutical composition containing the same is administered to a subject by intrathecal administration. As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

In some embodiments, a recombinant lysosomal enzyme protein or a pharmaceutical composition containing the same is administered to the subject by subcutaneous (i.e., beneath the skin) administration. For such purposes, the formulation may be injected using a syringe. However, other devices for administration of the formulation are available such as injection devices (e.g., the Inject-ease™ and Genject™ devices); injector pens (such as the GenPen™); needleless devices (e.g., MediJector™ and BioJector™); and subcutaneous patch delivery systems.

In some embodiments, intrathecal administration may be used in conjunction with other routes of administration (e.g., intravenous, subcutaneously, intramuscularly, parenterally, transdermally, or transmucosally (e.g., orally or nasally)).

The present invention contemplates single as well as multiple administrations of a therapeutically effective amount of a recombinant lysosomal enzyme protein or a pharmaceutical composition containing the same described herein. A recombinant HNS or a pharmaceutical composition containing the same can be administered at regular intervals, depending on the nature, severity and extent of the subject's condition (e.g., a lysosomal storage disease). In some embodiments, a therapeutically effective amount of a recombinant lysosomal enzyme protein or a pharmaceutical composition containing the same may be administered periodically at regular intervals (e.g., once every year, once every six months, once every five months, once every three months, bimonthly (once every two months), monthly (once every month), biweekly (once every two weeks), weekly, daily or continuously).

A recombinant lysosomal enzyme protein or a pharmaceutical composition containing the same can be formulated with a physiologically acceptable carrier or excipient to prepare a pharmaceutical composition. The carrier and therapeutic agent can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In some embodiments, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrrolidone, sodium saccharine, cellulose, magnesium carbonate, etc.

The composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof (e.g., a reduction in or elimination of the presence or incidence of "zebra bodies" or cellular vacuolization following the administration of the compositions of the present invention to a subject). Generally, the amount of a therapeutic agent (e.g., a recombinant lysosomal enzyme) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

EXAMPLES

Example 1. Development of CZE Analysis of Recombinant HNS

This example illustrates the initial development of CZE analysis of recombinant HNS protein.

Chemicals and Reagents

Sodium hydroxide solutions (1.0 N and 0.1 N) and ultra pure water were provided by Agilent Technologies (Wilmington, Del., USA). Tris-(hydroxymethyl)aminomethane hydrochloride (Tris-HCl) and Tris-(hydroxymethyl)aminomethane (Tris-base) were supplied by Sigma-Aldrich (St. Louis, Mo., USA). The background electrolyte buffer (BGE) was prepared by making 25 mM stock solutions of both Tris-HCl and Tris-base. Using a pH meter, the pH of Tris-HCl was adjusted to pH 8 using the Tris base solution. The solution was filtered through a 0.22 um nylon or Teflon filter and stored in a plastic bottle. Alkaline phosphatase and neuraminidase were purchased from Roche Diagnostics.

Sample Preparation

Human heparan-N-sulfatase (HNS) was produced in a human fibrosarcoma cell line. Purified HNS batches were obtained by a combination of various chromatographic steps. The protein was formulated in 5 mM Sodium Phosphate, 145 mM Sodium Chloride, pH 7.0 at a concentration of 15 mg/mL. Prior to CZE analysis, samples were diluted to approximately 1 mg/mL in 0.1×BGE. A negative peak on each electropherogram marked the electroosmotic flow (EOF) breakthrough which represents the position of solute migration which has a net charge of zero. This was confirmed by using mesityl oxide as a neutral marker which migrated in the same position (data not shown).

CZE Conditions

CZE was performed on an Agilent™ 7100 instrument equipped with a photo-diode array detector and ChemStation software from Agilent Technologies (Wilmington, Del., USA). Bare fused-silica capillaries columns (104 cm×50 μm id, L=112.5 cm) were supplied by Agilent Technologies (Wilmington, Del., USA). Prior to first use, the capillary was rinsed for 1 hour with 1.0 N NaOH, 5 minute with water and then 10 minute with 25 mM Tris, pH 8.0 (BGE). The capillary was stored overnight in BGE to provide optimal migration time precision. Samples were introduced into the anodic end of the capillary by pressure injection for 2 sec under 50 mbar pressure. The voltage was +30 kV generating a current of approximately 8 μA. The capillary temperature was 30° C. The detection wavelength was 200 nm with a bandpass of 8 nm. A reference wavelength was not used.

Data were collected with a peak width at <0.006 min (0.062 sec response time and 40 Hz). Between injections, the capillary was rinsed with water for 0.5 min, 0.1 N NaOH for 3 min, water for 0.5 min, and BGE for 6 min. For each sample, 3 separate injections were performed from a single preparation. The relative area for each peak was calculated by dividing the absolute area of the peak by the total absolute areas of all fourteen peaks. Reportable values consist of the average of triplicate injections. New buffer preparations were made for 5 of the 7 assays and a total of 4 different capillaries were used.

Recombinant human heparan-N-sulfatase (HNS) was produced in a human fibrosarcoma cell line, purified by a combination of various chromographic steps and formulated in 5 mM Sodium Phosphate, 145 mM Sodium Chloride, pH 7.0 at a concentration of 15 mg/mL. Prior to CZE analysis, samples were diluted to approximately 1 mg/ml in 0.1× BGEA purified HNS sample was analyzed by anion-exchange chromatography, which yielded a total of 7 individual peaks. capillary isoelectric focusing yielded 8 peaks over a pH gradient of 3-10 (data not shown); while capillary zone electrophoresis provided a partial separation of 14 discrete peaks at a pH of 8.0 (FIG. 7). As demonstrated in FIG. 1, traditional methods such as gel isoelectric focusing lack the level of sensitivity needed to quantitatively discern discrete, yet sometimes subtle, differences within the native-charge profile of recombinant proteins produced using commercial manufacturing methods.

Example 2. Evaluation of Experimental CZE Conditions in Determining Peak Separation Native HNS has a pI in the range of approx. 5.1-6.5 as determined by isoelectric focusing SDS-PAGE (data not shown). This rather broad pI range is a property common to glycoproteins (and human lysosomal enzymes in general) and is often the result of variations in charged terminal carbohydrate moieties such as sialic acid and mannose-6-phosphate (M6P), that result from post-translational modification. As demonstrated in FIG. 7, the use of CZE to evaluate the native-charge profile for HNS resulted in the separation of 14 discrete peaks. Several variables, such as pH, buffer composition, buffer strength and column length can all effect charge isoform separation and resolution. As such, each of these variables was tested to determine their overall effect on HNS characterization by CZE. In addition, such insight was used to determine assay tolerance and reproducibility.

Effect of Buffer Composition on Peak Separation

To determine the effects of buffer composition on HNS peak separation, CZE was performed on an Agilent™ 7100 instrument equipped with a photo-diode array detector and ChemStation software from Agilent Technologies (Wilmington, Del., USA), using purified recombinant HNS protein as described above. A bare fused-silica capillary column (104 cm×50 µm id, L=112.5 cm) was rinsed for 1 hour with 1.0 N NaOH, 5 minute with water and then 10 minute with 25 mM Tris, at pH 8.0. Samples were introduced into the anodic end of the capillary by pressure injection for 2 sec under 50 mbar pressure. The voltage was +30 kV generating a current of approx. 8 µA. The capillary temperature was 30 C. The detection wavelength was 200 nm with a bandpass of 8 nm. A reference wavelength was not used. Data were collected with a peakwidth at <0.006 min (0.062 sec response time)(40 Hz). Between injections, the capillary was rinsed with water for 0.5 min, 0.1 N NaOH for 3 min and water for 0.5 min.

For the experiment, HNS peak separation was evaluated using the following buffers equilibrated to pH 8.0: 25 mM Tris, 15 mM Borate, 25 mM Borate, 25 mM HEPES, 25 mM Gly-Gly, and Phosphate (Table 3). The data suggests, that HNS separation by CZE at pH 8.0 using Tris buffer, resulted in the good separation, detection and resolution of each HNS charge isoform. While HEPES and Gly-Gly buffers both produced a HNS charge isoform separation comparable to that of Tris, detection was reduced due to each buffer's UV absorption at 200 nm wavelength, resulting in a high background signal. Borate and Phosphate buffer both displayed a reduced level of HNS isoform separation as well as poor peak resolution. Several adjuvants were also tested for their ability to further enhance charge isoform separation in 25 mM Tris (Data not shown). The data suggest that the addition of 25 mM sodium chloride, urea, hydroxyethylcellulose or EDTA to 25 mM Tris buffer, reduced peak resolution and isoform separation.

TABLE 3

Summary of Different Buffer Evaluation

| Parameter | | Result |
|---|---|---|
| Buffer Type | Tris | 14 plus resolved peaks |
| | Borate | 15 and 25 mM Borate, pH 8.0 were evaluated with 15 mM giving the best resolution. Total peak resolution was less than with Tris |
| | Hepes | 25 mM Hepes, pH 8.0; comparable resolution with Tris. |
| | Gly-Gly | 25 mM Gly-Gly, pH 8.0; Total peak resolution was less than with Tris |
| | Phosphate | Interfered with background signal |

Effect of Buffer Concentration on Peak Separation

Based on the findings above, additional studies were performed to explore the effect of Tris buffer concentration on HNS peak separation. Purified recombinant HNS, as described above, was subjected to CZE using an Agilent™ 7100 instrument equipped with a photo-diode array detector and ChemStation software from Agilent Technologies (Wilmington, Del., USA). A bare fused-silica capillary column (104 cm×50 µm id, L=112.5 cm) was rinsed for 1 hour with 1.0 N NaOH, 5 minute with water and then 10 minute with the desired experimental Tris buffer concentration, equilibrated to pH 8.0. Samples were introduced into the anodic end of the capillary by pressure injection for 2 sec under 50 mbar pressure. The voltage was +30 kV generating a current of approx. 8 µA. The capillary temperature was 30 C. The detection wavelength was 200 nm with a bandpass of 8 nm. A reference wavelength was not used. Data were collected with a peakwidth at <0.006 min (0.062 sec response time)(40 Hz). Between injections, the capillary was rinsed with water for 0.5 min, 0.1 N NaOH for 3 min and water for 0.5 min.

Figure 2A:
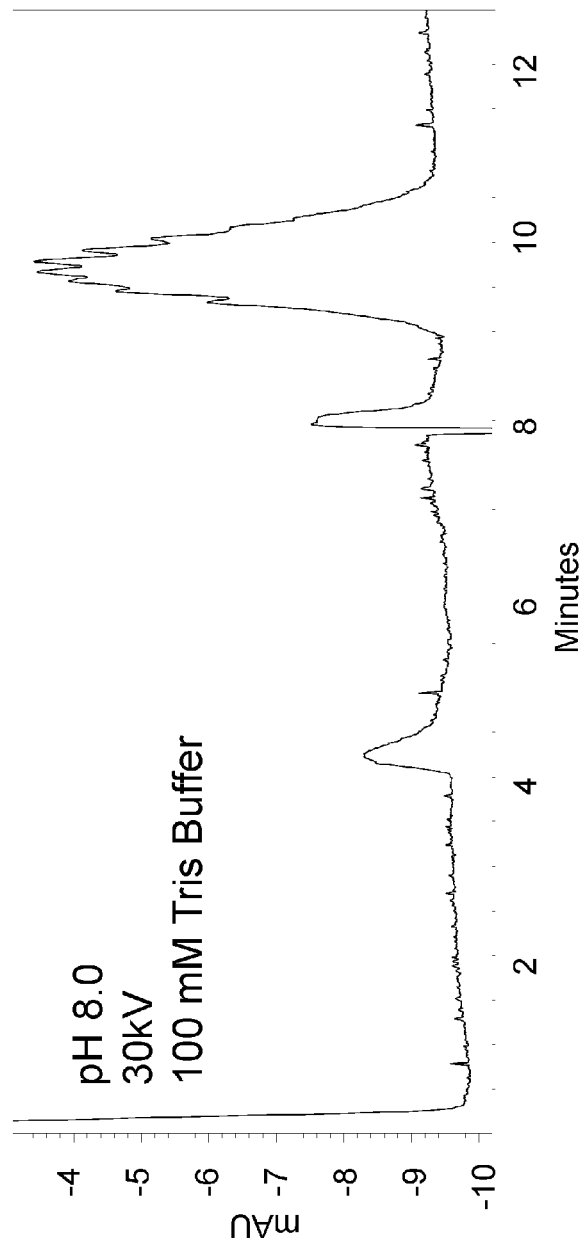
FIG. 2A-2C. demonstrates the effect of buffer strength on peak separation during capillary zone electrophoresis. The charge profile for recombinant HNS was analyzed by capillary zone electrophoresis using Tris buffer at (2A) 100 mM; (2B) 50 mM and (2C) 25 mM concentration.
Figure 2B:
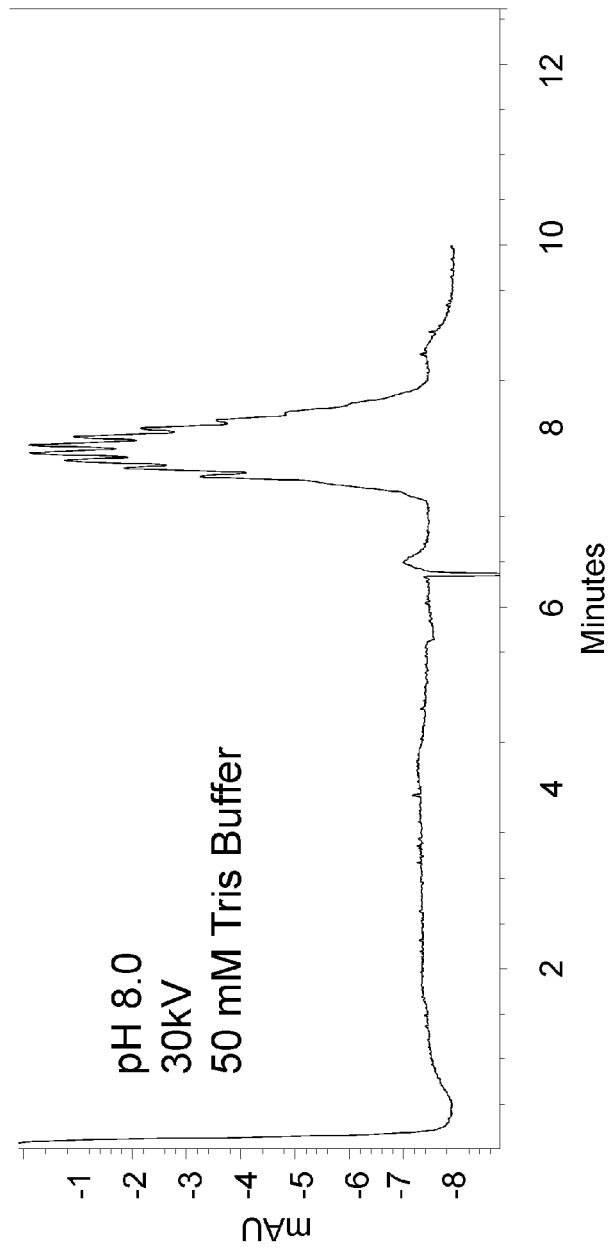
Figure 2C:
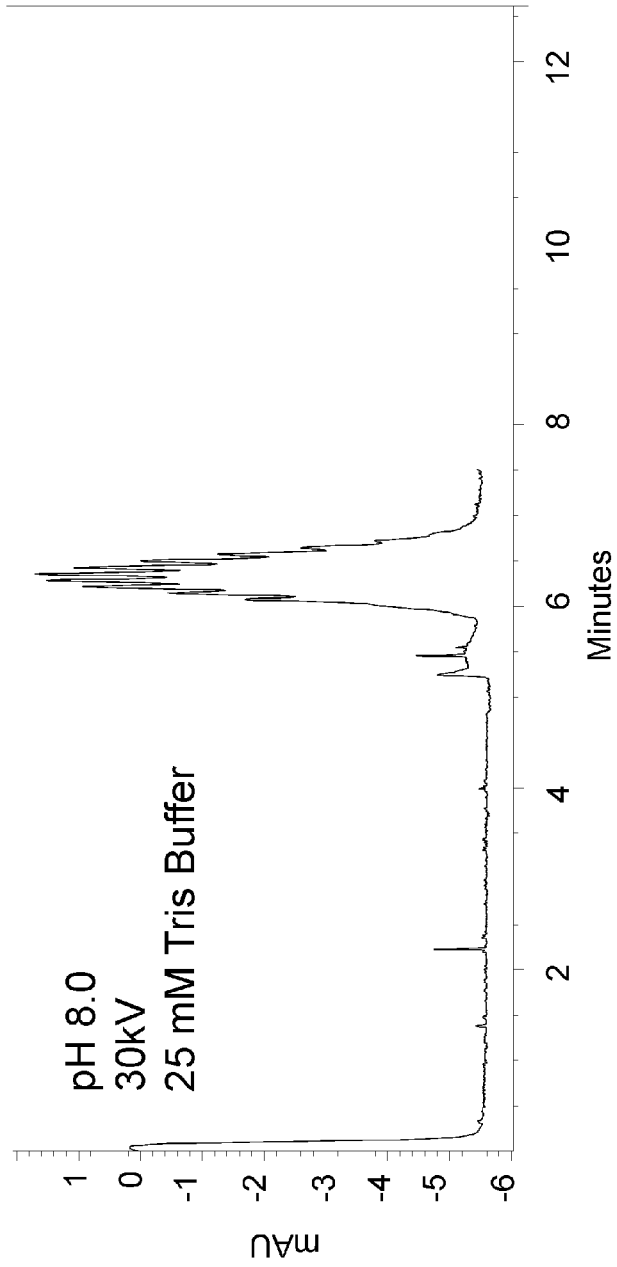

For the initial experiment, HNS peak separation was evaluated over a broad pH range using the following reaction conditions: 100 mM Tris Buffer at pH 8.0 (FIG. 2A), 50 mM Tris Buffer at pH 8.0 (FIG. 2B), and 25 mM Tris Buffer at pH 8.0 (FIG. 2C). The data suggest, that HNS separation by CZE using Tris buffer at pH 8.0, lead to a greater separation in charge isoforms close to 25 mM buffer concentration. As indicated in FIGS. 2A and 2B, at Tris buffer concentrations higher than 25 mM, HNS separation was reduced leading to a poor resolution of individual isoform peak separation.

Figure 3:
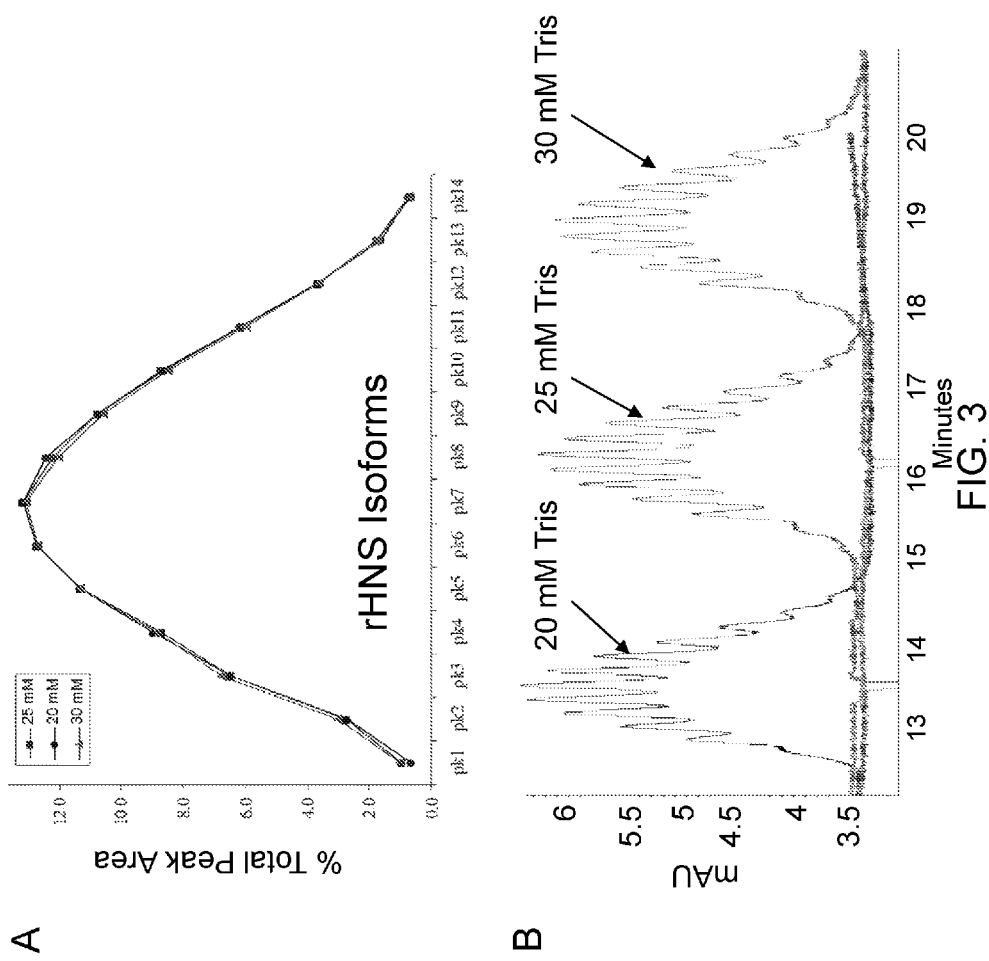
FIG. 3. depicts the charge profile for recombinant HNS as analyzed by (B) capillary zone electropherograms and (A) relative peak area, using Tris buffer at pH 8.0 over a range of buffer concentrations.

Based on these initial findings, additional studies were performed to evaluate CZE assay tolerance for minor variations in Tris buffer concentration, during HNS characterization. Using the same CZE conditions described above, purified recombinant HNS proteins was analyzed by CZE using 20 mM, 25 mM, or 30 mM Tris buffer (FIG. 3B). As demonstrated in FIG. 3, minor fluctuations in Tris buffer concentration still provided robust peak separation (B) along with sharp resolution of 14 distinct charge isoforms (A). This data strongly suggests, that the use of CZE for determining HNS charge profile is both a robust and sensitive methods. Furthermore, these findings also suggest, that a range of at least 20-30 mM Tris buffer may be used for CZE characterization of human HNS. Although there is a slight loss of resolution seen at 20 mM (see early peaks) (FIG. 3B) there appears to be no effect on the peak quantitation. These data demonstrate the method is robust within 20% of target buffer concentration.

Effect of pH on Peak Separation

To determine the effects of pH on HNS peak separation, CZE was performed on an Agilent™ 7100 instrument equipped with a photo-diode array detector and ChemStation software from Agilent Technologies (Wilmington, Del., USA), using purified recombinant HNS protein as described above. A bare fused-silica capillary column (104 cm×50 μm id, L=112.5 cm) was rinsed for 1 hour with 1.0 N NaOH, 5 minute with water and then 10 minute with 25 mM Tris, at the desired experimental pH. Samples were introduced into the anodic end of the capillary by pressure injection for 2 sec under 50 mbar pressure. The voltage was +30 kV generating a current of approx. 8 μA. The capillary temperature was 30 C. The detection wavelength was 200 nm with a bandpass of 8 nm. A reference wavelength was not used. Data were collected with a peakwidth at <0.006 min (0.062 sec response time)(40 Hz). Between injections, the capillary was rinsed with water for 0.5 min, 0.1 N NaOH for 3 min and water for 0.5 min.

For the experiment, HNS peak separation was evaluated over a broad range of pH conditions: Tris Buffer at pH 8.5 (FIG. 4A), pH 8.0 (FIG. 4B), pH 7.5 (FIG. 4C) and pH 7.0 (FIG. 4D). These data suggest, that HNS separation by CZE at pH 8.0 results in better charge separation with the greatest number of distinguishable isoform peaks. The data also suggests, that for human HNS, separation was all but lost as the pI of the more basic isoforms are approached around pH 7.0 (FIG. 4D)

Figure 5:
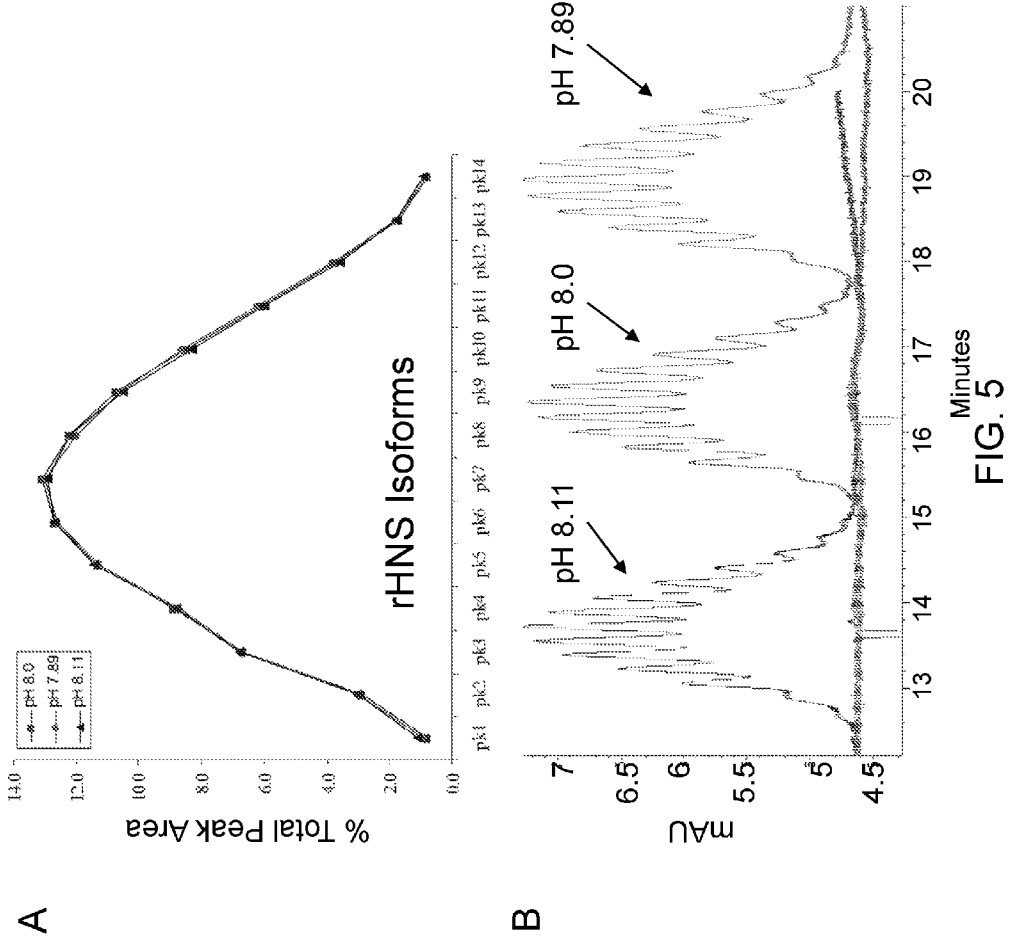
FIGS. 5A&B. depicts the charge profile for recombinant HNS as analyzed by (B) capillary zone electropherograms and (A) relative peak area, using Tris buffer at 25 mM concentration over of varying pH.

Based on these initial findings, additional studies were performed to evaluate CZE assay tolerance for minor variations in pH, during HNS characterization. Using the same CZE conditions described above, purified recombinant HNS proteins was analyzed by CZE using 25 mM Tris buffer equilibrated to a pH of 7.89, 8.0 or 8.11 (FIG. 5B). As demonstrated, minor fluctuations around pH 8.0 still resulted in a robust peak separation (FIG. 5B) along with sharp resolution of 14 distinct charge isoforms (FIG. 5A). This data strongly suggests, that the use of CZE for determining HNS charge profile is both a robust and sensitive methods. Furthermore, these findings also suggest, that a pH range of at least 7.89-8.11 in 25 mM Tris buffer may be used for CZE characterization of human HNS.

Effect of Capillary Composition and Length on Peak Separation

To determine the effects of capillary composition and length on HNS peak separation, CZE was performed on an Agilent™ 7100 instrument equipped with a photo-diode array detector and ChemStation software from Agilent Technologies (Wilmington, Del., USA), using purified recombinant HNS protein as described above. A polyvinyl alcohol (PVA) or bare fused-silica capillary column (104 cm×50 μm id) either 72 of 104 cm in length was rinsed for 1 hour with 1.0 N NaOH, 5 minute with water and then 10 minute with 25 mM Tris, pH 8.0. Samples were introduced into the anodic end of the capillary by pressure injection for 2 sec under 50 mbar pressure. The voltage was +30 kV generating a current of approx. 8 μA. The capillary temperature was 30 C. The detection wavelength was 200 nm with a bandpass of 8 nm. A reference wavelength was not used. Data were collected with a peakwidth at <0.006 min (0.062 sec response time)(40 Hz). Between injections, the capillary was rinsed with water for 0.5 min, 0.1 N NaOH for 3 min and water for 0.5 min.

Figure 6:
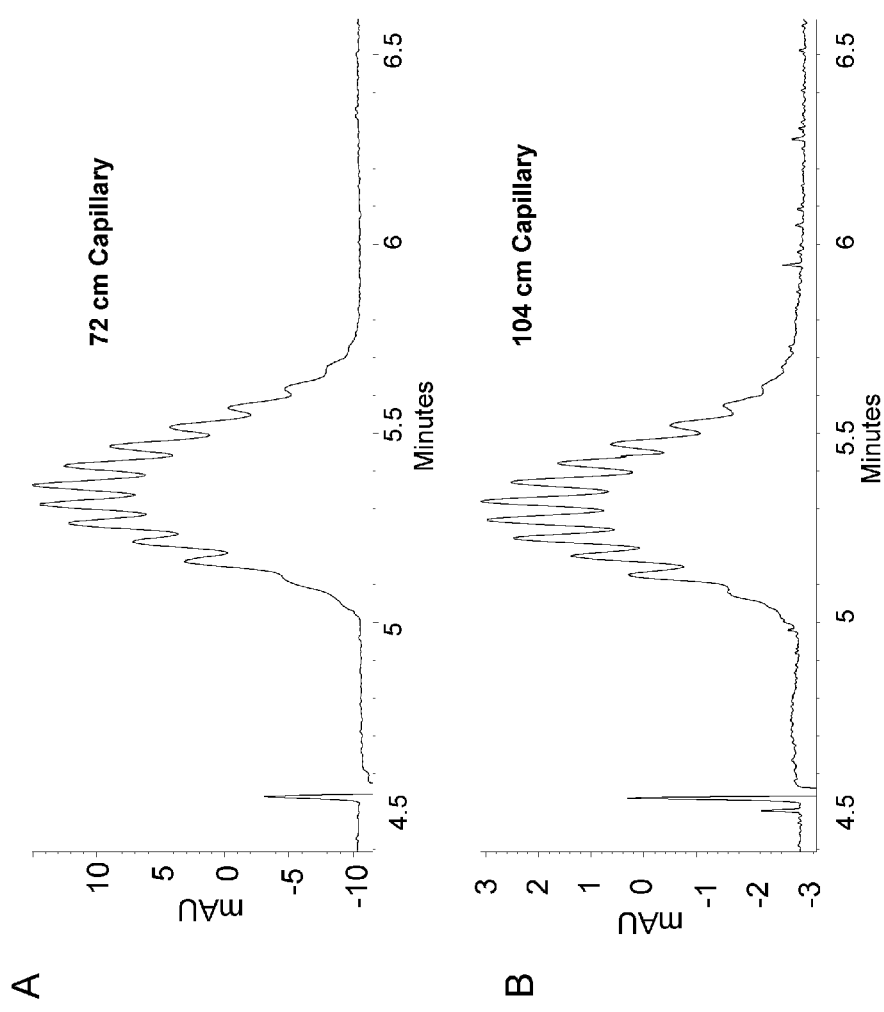
FIG. 6. demonstrates the effect of capillary length on peak separation during capillary zone electrophoresis. The charge profile for recombinant HNS was analyzed by capillary zone electrophoresis using bare fused-silica capillary columns of either (A) 72 cm or (B) 104 cm in length.

Preliminary experiments revealed, that unlike a bare fused-silica capillary column, a polyvinyl alcohol (PVA) coated capillary column resulted in a reduced level of separation and poor resolution of each of the 14 individual charge isoforms. Suggesting, that separation was retarded due to interactions between the protein and the PVA coating of the column, indicating that for human HNS glycoform separation, repulsion between the negatively charged protein and the capillary wall may be essential for optimal separation. It is often best to use a short capillary column and optimize the buffer and buffer additives. For HNS, this approach was not possible. As a result, capillary length was evaluated to help optimize HNS isoform separation. The longest length of capillary that would fit in the instrument's cassette, 104 cm, was employed. Despite the long length of the capillary, the separation was complete in 16 min due to the robust electroosmotic flow (EOF). A normalized comparison between the separation on a 72 cm and 104 cm capillary is shown in FIG. 6. While the run time increased from about 6 to 14 min, the resolution was improved on the longer capillary despite the reduced field strength.

Example 3. Repeatability and Precision

For this example, the CZE approach described above, was examined for repeatability and precision in characterizing HNS, in order to evaluate its potential quantitative analysis and characterization of native-charge heterogeneity of recombinant HNS during product development. For the example, repeatability and precisions were assayed by measuring CZE performance (as a function of migration time and relative peak area) and the ability of the method to discriminate subtle variations of glycoforms distribution between similar and different manufactured lots of recombinant HNS.

Figure 8:
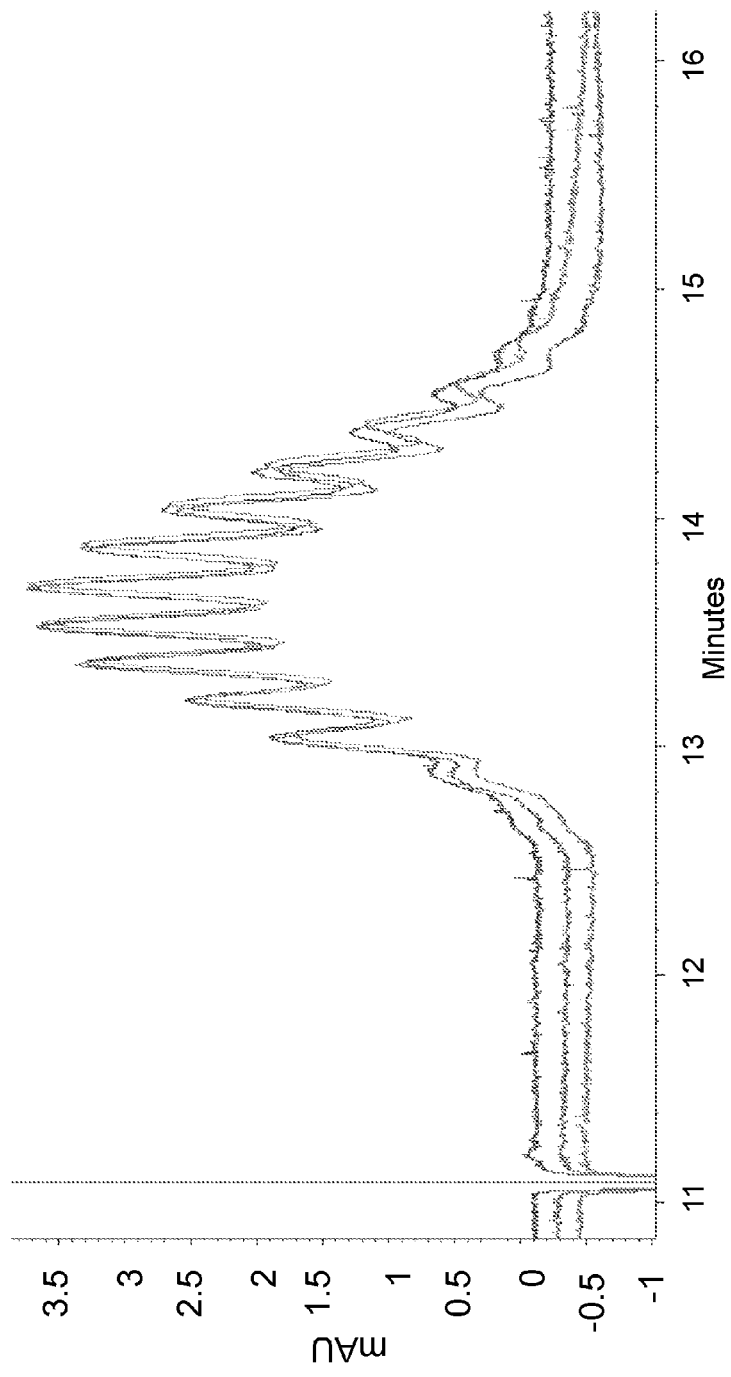
FIG. 8. depicts the run-to-run repeatability for the charge profile of recombinant HNS enzyme analyzed by capillary zone electrophoresis, assayed using triplicate injections for the same manufactured lot.

Using a common manufactured lot of recombinant human HNS (Lot A), both run-to-run and day-to-day repeatability of the relative peak areas and migration times were evaluated. The run-to-run repeatability is shown in FIG. 8 for triplicate runs. Since it was necessary to compare the glycoform populations of different batches despite the passage time, the relative and absolute migration times from 7 independent measurements run in triplicate over a period of four months (FIG. 9) were calculated and are displayed in Table 4.

TABLE 4

Relative and Absolute Migration Times

| Isoform | % Peak Area | | MT | | RMT | |
| --- | --- | --- | --- | --- | --- | --- |
| | Mean | RSD %[a] | Mean | RSD %[a] | Mean | RSD %[a] |
| Iso-1 | 1.2 | 5.0 | 12.9 | 0.8 | 1.15 | 0.3 |
| Iso-2 | 2.9 | 4.0 | 13.1 | 0.8 | 1.16 | 0.3 |
| Iso-3 | 7.1 | 1.1 | 13.2 | 0.9 | 1.18 | 0.4 |
| Iso-4 | 8.9 | 1.1 | 13.4 | 0.9 | 1.19 | 0.4 |
| Iso-5 | 12.0 | 1.2 | 13.5 | 0.9 | 1.21 | 0.4 |
| Iso-6 | 13.2 | 1.0 | 13.7 | 0.9 | 1.22 | 0.4 |
| Iso-7 | 13.6 | 0.9 | 13.9 | 0.9 | 1.24 | 0.4 |
| Iso-8 | 12.3 | 0.6 | 14.1 | 0.9 | 1.25 | 0.4 |
| Iso-9 | 10.5 | 0.9 | 14.2 | 0.9 | 1.27 | 0.4 |
| Iso-10 | 8.0 | 1.1 | 14.4 | 0.9 | 1.28 | 0.4 |
| Iso-11 | 5.5 | 1.4 | 14.6 | 0.9 | 1.30 | 0.4 |
| Iso-12 | 3.1 | 2.8 | 14.8 | 1.0 | 1.31 | 0.4 |
| Iso-13 | 1.3 | 7.4 | 14.9 | 1.0 | 1.33 | 0.5 |
| Iso-14 | 0.4 | 23.2 | 15.1 | 0.9 | 1.35 | 0.3 |

MT (Migration time);
RMT (Relative Migration Time)

Figure 9:
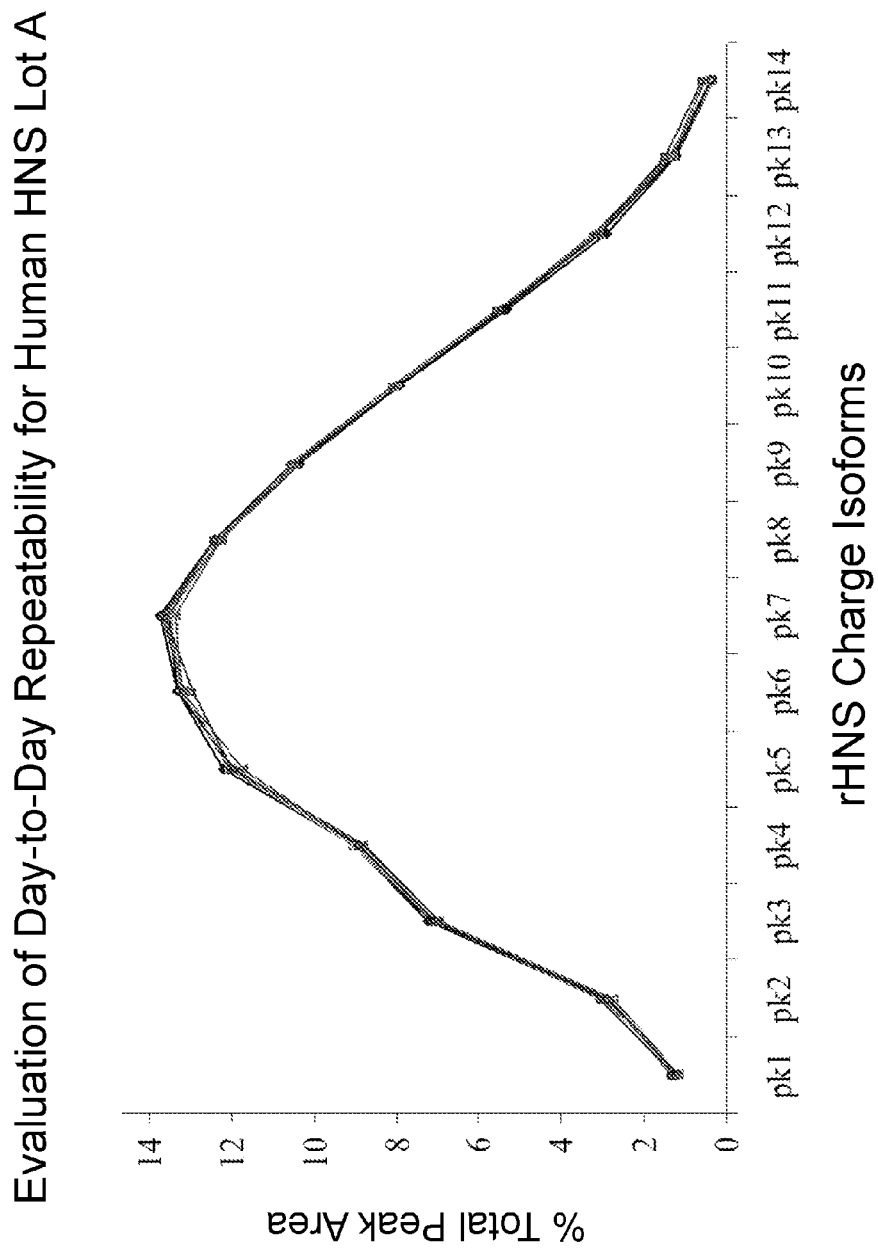
FIG. 9. depicts the day-to-day repeatability for the charge profile of recombinant HNS enzyme. Recombinant human HNS enzyme was analyzed by capillary zone electrophoresis for seven independent experiments run over the course of four months. Data was expressed as relative migration time (RMT) and relative peak area (%) to determine any change in reproducibility.

While the absolute migration times ($t_m$) were all less than or equal to 1%, relative migration time (RMT) was preferred ($t_m/t_{EOF}$) as the reporting parameter. Since the peak widths were narrow and the migration times differed only by about 10 sec, the RMT better assured correct peak identification. The RMTs ranged from 0.3-0.5%. The precision of the relative peak areas (peak area percentages) are shown in Table 3. The relative standard deviation (RSD) of relative area ranged from 0.6% to 2.8% for isoforms 3-12, 4.0% to 5.0% for isoforms 1 and 2, and 7.4% to 23.2% for isoforms 13 and 14. The data suggests that higher RSD percentage for isoforms 1-2 and 13-14 may be attributed to their low relative areas. The data was also assess by plotting the total peak area % of each of the 14 HNS isoforms, for the day-to-day comparison data, were also calculated and are displayed in Table 5. FIG. 9 demonstrates little to no variation in the total peak area or each of the 14 isoforms, over the four month period. Taken together, these data strongly suggest that the use of CZE, in accordance with the methods and conditions described above, can be used to accurately characterize HNS glycoforms in a precise and reproducible fashion.

TABLE 5

Precision of relative peak areas (%).

| Isoform | Mean | RSD %[a] | Min | Max |
| --- | --- | --- | --- | --- |
| Iso-1 | 1.2 | 5.0 | 1.2 | 1.3 |
| Iso-2 | 2.9 | 4.0 | 2.8 | 3.1 |
| Iso-3 | 7.1 | 1.1 | 7.0 | 7.2 |
| Iso-4 | 8.9 | 1.1 | 8.8 | 9.1 |
| Iso-5 | 12.0 | 1.2 | 11.7 | 12.2 |
| Iso-6 | 13.2 | 1.0 | 12.9 | 13.3 |
| Iso-7 | 13.6 | 0.9 | 13.4 | 13.7 |
| Iso-8 | 12.3 | 0.6 | 12.2 | 12.4 |
| Iso-9 | 10.5 | 0.9 | 10.3 | 10.6 |
| Iso-10 | 8.0 | 1.1 | 7.9 | 8.1 |
| Iso-11 | 5.5 | 1.4 | 5.3 | 5.5 |
| Iso-12 | 3.1 | 2.8 | 2.9 | 3.2 |
| Iso-13 | 1.3 | 7.4 | 1.2 | 1.5 |
| Iso-14 | 0.4 | 23.2 | 0.3 | 0.6 |

[a]RSD were calculated from n = 7 analysis. Each analysis was performed on a different day over a period of 4 months. Most analyses used fresh buffer preparations and were performed on 3 different capillaries.

Example 4. CZE Characterization of HNS for Identifying Manufacturing Variation

Studies were also performed to evaluate methods for using CZE to carryout quantitative HNS characterization, such as the identification of glycoforms and heterogeneous native charge structures, during the manufacture of human recombinant HNS. Generation of quantitive, reproducible characterization data, may be used to monitor/optimize production methods, as well as standardize commercial product production in accordance with FDA guidelines.

Characterization of Lot-to-Lot Variation

For this example, the CZE approach described above, was examined for characterizing HNS, in order to evaluate its potential quantitative analysis and characterization of native-charge heterogeneity of recombinant HNS between different lots of the same manufacturing process.

Purified recombinant HNS enzyme was produced in two separate manufacturing runs, using the same downstream manufacturing process. Capillary zone electrophoresis was performed on an Agilent™ 7100 instrument equipped with a photo-diode array detector and ChemStation software from Agilent Technologies (Wilmington, Del., USA). A bare fused-silica capillary column (104 cm×50 µm id, L=104 cm) was rinsed for 1 hour with 1.0 N NaOH, 5 minute with water and then 10 minute with 25 mM Tris buffer, equilibrated to pH 8.0. Samples were introduced into the anodic end of the capillary by pressure injection for 2 sec under 50 mbar pressure. The voltage was +30 kV generating a current of approx. 8 µA. The capillary temperature was 30° C. The detection wavelength was 200 nm with a bandpass of 8 nm. A reference wavelength was not used. Data were collected with a peakwidth at <0.006 min (0.062 sec response time) (40 Hz). Between injections, the capillary was rinsed with water for 0.5 min, 0.1 N NaOH for 3 min and water for 0.5 min.

Figure 10A:
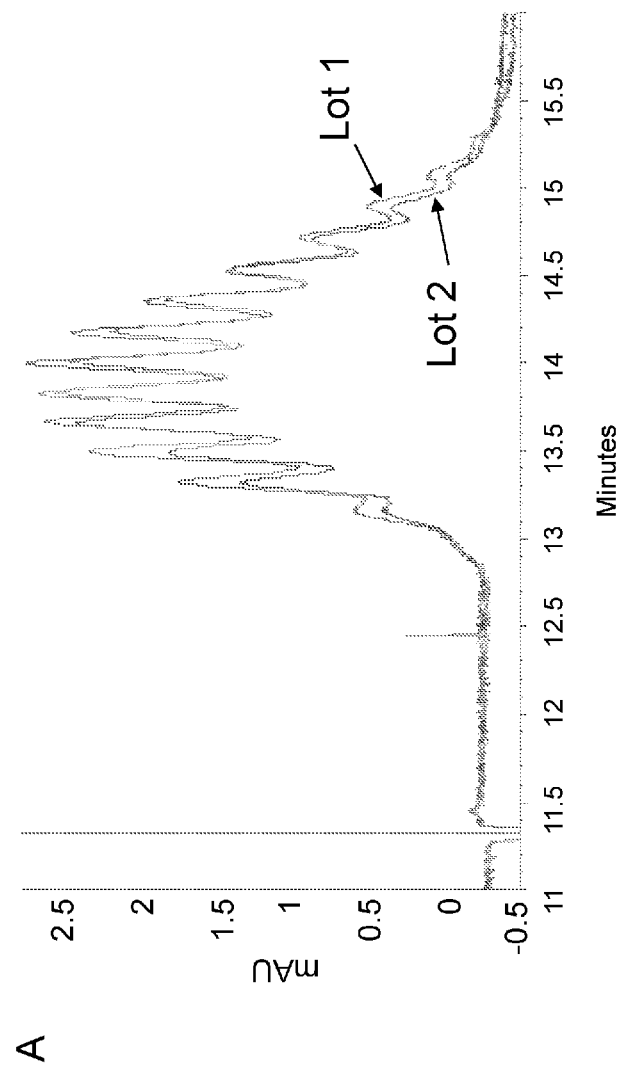
FIGS. 10A & 10B. depicts the charge profile for two different lots of recombinant HNS enzyme, produced using the same manufacturing process, analyzed by (10A) capillary zone electrophoresis to determine the (10B) relative peak area (%) for 14 different HNS charge isoforms.
Figure 10B:
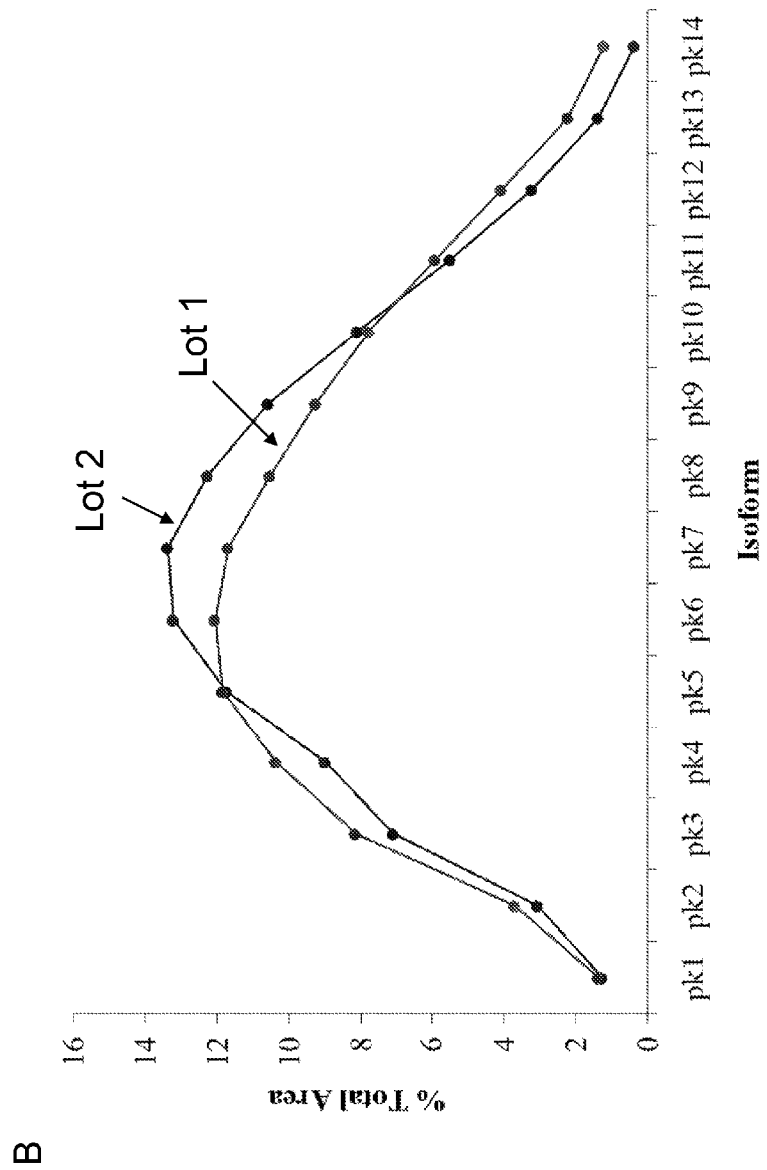

FIG. 10A shows the overlaid electropherograms of each manufactured lot (Lot 1 and Lot 2). The data suggests, that while the same number of native charge isoform peaks are present in both manufacturing lots, subtle differences in the peak distribution or "manufacturing fingerprint" are present. These differences were further delineated by calculating relative peak area (represented as percent total area) for each manufactured lot (FIG. 10B). The relative peak area data for Lot 1 and 2 was compared to characterized reference Lot 189 (FIG. 7) and displayed in Table 6.

TABLE 6

Comparison of Relative Peak Areas (%) for Different HNS Lots

| | Run 1 | | |
| --- | --- | --- | --- |
| Isoform | Ref. Lot | Lot 1 | Lot 2 |
| Iso-x | nd | nd | nd |
| Iso-y | nd | nd | nd |
| Iso-1 | 1.3 | 1.4 | 1.9 |
| Iso-2 | 3.1 | 3.7 | 4.1 |
| Iso-3 | 7.1 | 8.1 | 9.6 |
| Iso-4 | 9.0 | 10.3 | 10.2 |
| Iso-5 | 11.7 | 11.8 | 14.0 |
| Iso-6 | 13.2 | 12.0 | 13.8 |
| Iso-7 | 13.4 | 11.7 | 13.0 |
| Iso-8 | 12.2 | 10.5 | 11.0 |
| Iso-9 | 10.6 | 9.3 | 8.7 |
| Iso-10 | 8.1 | 7.7 | 6.2 |
| Iso-11 | 5.5 | 5.9 | 4.0 |
| Iso-12 | 3.2 | 4.1 | 2.2 |

TABLE 6-continued

Comparison of Relative Peak Areas (%) for Different HNS Lots

| | Run 1 | | |
|---|---|---|---|
| Isoform | Ref. Lot | Lot 1 | Lot 2 |
| Iso-13 | 1.4 | 2.2 | 0.8 |
| Iso-14 | 0.4 | 1.2 | 0.3 |

Ref. Lot (HNS manufacturing lot 189), Lot 1 and 2 (Two different manufacturing lots of human recombinant HNS produced using the same downstream purification)

The analytical power of using CZE for HNS characterization was tested by examining differences in charge isoform detection levels for independent HNS lots using IEF-SDS PAGE and CZE. For the experiment, four different HNS manufacturing lots, each manufactured with the same downstream purification method, were tested. Capillary zone electrophoresis was performed on an Agilent™ 7100 instrument equipped with a photo-diode array detector and ChemStation software from Agilent Technologies (Wilmington, Del., USA). A bare fused-silica capillary column (104 cm×50 µm id, L=104 cm) was rinsed for 1 hour with 1.0 N NaOH, 5 minute with water and then 10 minute with 25 mM Tris buffer, equilibrated to pH 8.0. Samples were introduced into the anodic end of the capillary by pressure injection for 2 sec under 50 mbar pressure. The voltage was +30 kV generating a current of approx. 8 µA. The capillary temperature was 30° C. The detection wavelength was 200 nm with a bandpass of 8 nm. A reference wavelength was not used. Data were collected with a peakwidth at <0.006 min (0.062 sec response time)(40 Hz). Between injections, the capillary was rinsed with water for 0.5 min, 0.1 N NaOH for 3 min and water for 0.5 min. IEF-SDS PAGE was performed using standard molecular biology techniques, know to those skilled in the art.

Figure 11:
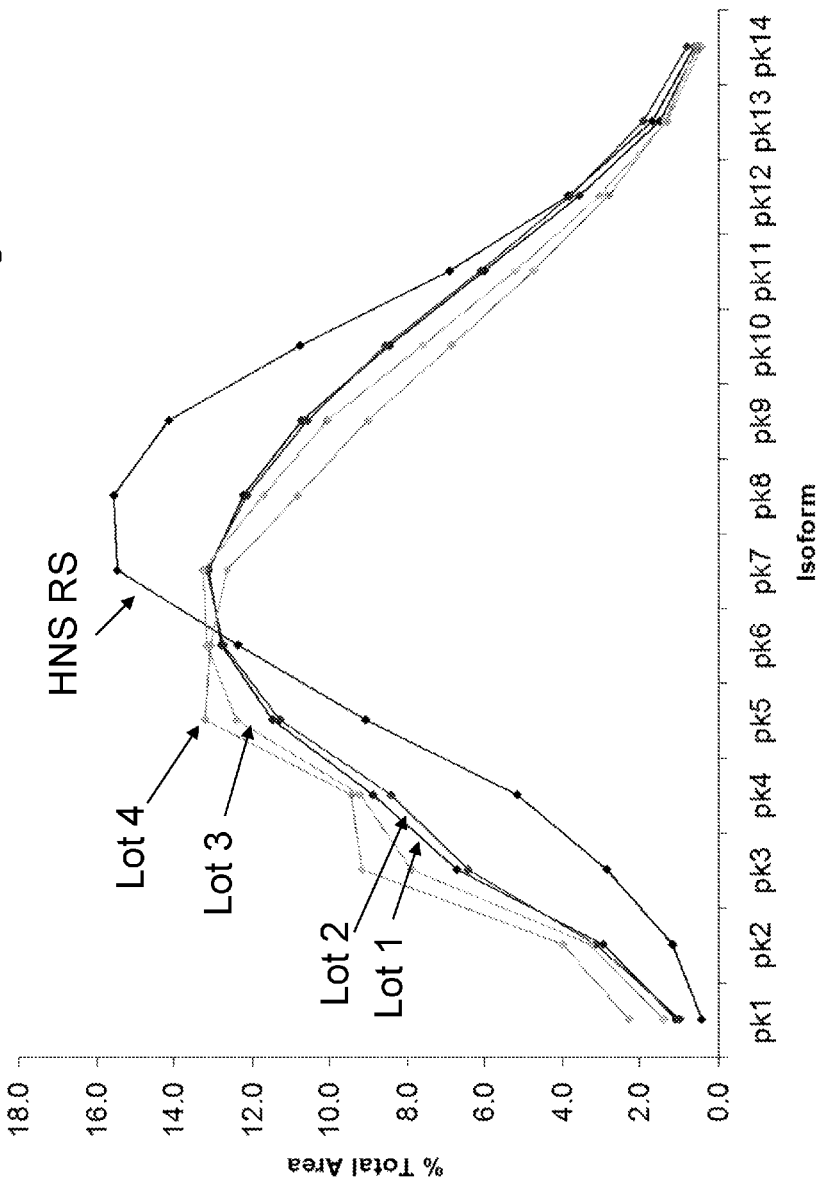
FIG. 11. depicts the charge profile for four different lots of recombinant HNS enzyme, produced using the same manufacturing process and analyzed by capillary zone electrophoresis to determine the relative peak area (%) for 14 different HNS charge isoforms.

FIG. 11 shows the overlaid electropherograms of each manufactured lot (Lot 1, 2, 3 and 4) compared to a characterized HNS manufacturing reference standard (RS). The data suggests, that while the same number of native charge isoform peaks are present in both manufacturing lots, differences in peak distribution or "manufacturing fingerprint" are present. These differences were quantitatively confirmed, by calculating relative peak area (represented as percent total area) for each manufactured lot and are displayed in Table 7.

TABLE 7

Comparison of Relative Peak Areas (%) for Different HNS Lots

| Isoform | HNS RS | Lot 1 | Lot 2 | Lot 3 | Lot 4 |
|---|---|---|---|---|---|
| Iso-1 | 0.4 | 1.1 | 1.0 | 1.4 | 2.3 |
| Iso-2 | 1.2 | 3.0 | 3.1 | 3.3 | 4.0 |
| Iso-3 | 2.9 | 6.7 | 6.4 | 7.9 | 9.2 |
| Iso-4 | 5.1 | 8.9 | 8.4 | 9.2 | 9.4 |
| Iso-5 | 9.1 | 11.5 | 11.3 | 12.4 | 13.2 |
| Iso-6 | 12.4 | 12.8 | 12.7 | 13.1 | 13.0 |
| Iso-7 | 15.5 | 13.1 | 13.2 | 13.3 | 12.7 |
| Iso-8 | 15.6 | 12.2 | 12.1 | 11.7 | 10.8 |
| Iso-9 | 14.2 | 10.7 | 10.6 | 10.1 | 9.0 |
| Iso-10 | 10.7 | 8.4 | 8.6 | 7.6 | 6.8 |
| Iso-11 | 6.9 | 6.0 | 6.1 | 5.2 | 4.7 |
| Iso-12 | 3.8 | 3.6 | 3.8 | 3.1 | 2.8 |
| Iso-13 | 1.7 | 1.5 | 1.9 | 1.3 | 1.4 |
| Iso-14 | 0.6 | 0.5 | 0.8 | 0.4 | 0.6 |

HNS RS (HNS manufacturing lot 189), Lot 1, 2, 3 and 4 (Four different manufacturing lots of human recombinant HNS produced using the same downstream purification)

The differences in HNS native charge distribution demonstrated using CZE were not observed using standard IEF-SDS PAGE, give the poor resolution and subjective nature of the assay (Data not shown). Taken together, these data demonstrate that the use of CZE in characterizing HNS allows for mathematically quantifiable differences between manufactured lots. Furthermore, it strongly suggests that given the peak separation and resolution properties of CZE in characterizing HNS charge isoforms, the approach is able to discern subtle differences in the heterogeneous HNS population that may not be readily apparent in other analytical approaches.

Characterization of HNS During Manufacturing Stages

The ability to assay changes in HNS native charge isoforms during different stages of the same manufacturing process was also tested. Purified recombinant HNS enzyme was produced in two separate manufacturing runs. Samples were collected prior to the start of the downstream purification and upon completion of the manufacturing process. Capillary zone electrophoresis was performed on an Agilent™ 7100 instrument equipped with a photo-diode array detector and ChemStation software from Agilent Technologies (Wilmington, Del., USA). A bare fused-silica capillary column (104 cm×50 µm id, L=104 cm) was rinsed for 1 hour with 1.0 N NaOH, 5 minute with water and then 10 minute with 25 mM Tris buffer, equilibrated to pH 8.0. Samples were introduced into the anodic end of the capillary by pressure injection for 2 sec under 50 mbar pressure. The voltage was +30 kV generating a current of approx. 8 µA. The capillary temperature was 30° C. The detection wavelength was 200 nm with a bandpass of 8 nm. A reference wavelength was not used. Data were collected with a peakwidth at <0.006 min (0.062 sec response time)(40 Hz). Between injections, the capillary was rinsed with water for 0.5 min, 0.1 N NaOH for 3 min and water for 0.5 min.

Figure 12A:
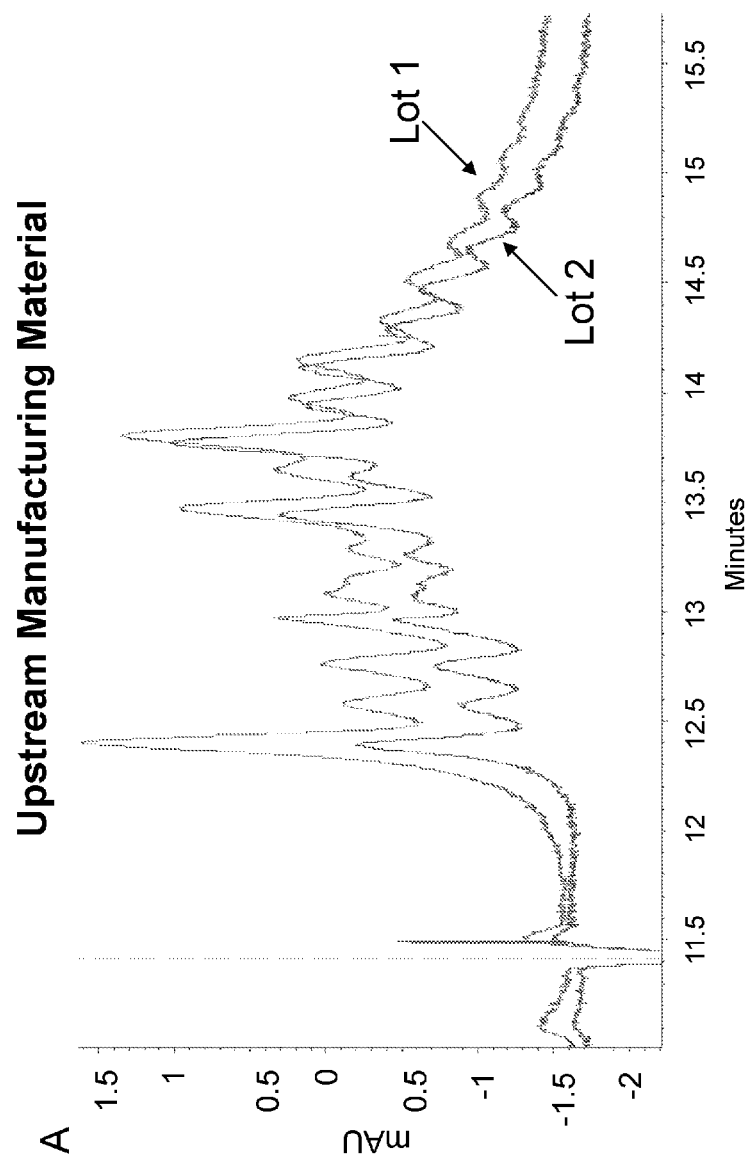
FIGS. 12A & 12B. depicts the charge profile for two different lots of recombinant HNS enzyme, produced using the same manufacturing process and analyzed by capillary zone electrophoresis (12A) early on and (12B) at the end of the manufacturing process.
Figure 12B:
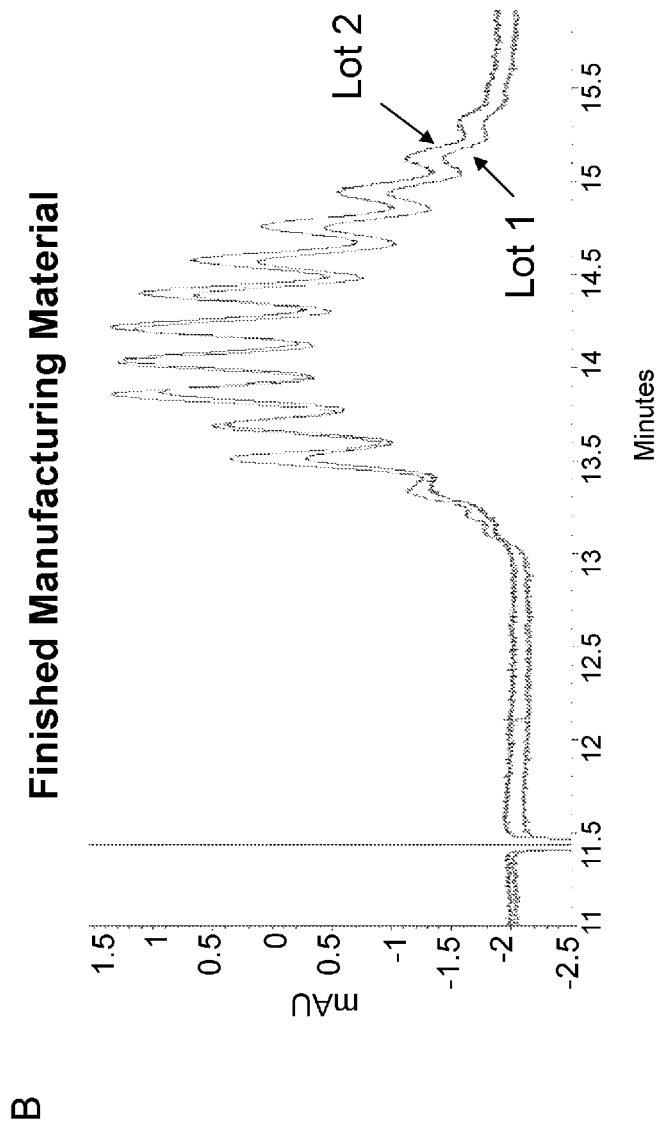

FIGS. 12 A and B show the overlaid electropherograms of each manufactured lot (Lot 1 and 2) prior to (A) and following (B) downstream purification. The data demonstrates differences in the native charge profile for NHS during the various stages of the manufacturing process. This suggests that CZE may be used to monitor changes in HNS heterogeneity during manufacturing and in the file finished product. It also suggests, CZE as a functional readout, it may be used to optimized and modify the manufacturing steps to control the HNS charge profile for the finished product.

Characterization of HNS Produced from Different Manufacturing Processes

Differences in charge profile associated with different manufacturing processes were also examined. For the experiment, purified recombinant HNS enzyme was produced using two different downstream manufacturing processes, in which alternative buffer compositions were used. Capillary zone electrophoresis was performed on an Agilent™ 7100 instrument equipped with a photo-diode array detector and ChemStation software from Agilent Technologies (Wilmington, Del., USA). A bare fused-silica capillary column (104 cm×50 µm id, L=104 cm) was rinsed for 1 hour with 1.0 N NaOH, 5 minute with water and then 10 minute with 25 mM Tris buffer, equilibrated to pH 8.0. Samples were introduced into the anodic end of the capillary by pressure injection for 2 sec under 50 mbar pressure. The voltage was +30 kV generating a current of approx. 8 µA. The capillary temperature was 30° C. The detection wavelength was 200 nm with a bandpass of 8 nm. A reference wavelength was not used. Data were collected with a peakwidth at <0.006 min (0.062 sec response time)(40 Hz). Between injections, the capillary was rinsed with water for 0.5 min, 0.1 N NaOH for 3 min and water for 0.5 min.

Figure 13A:
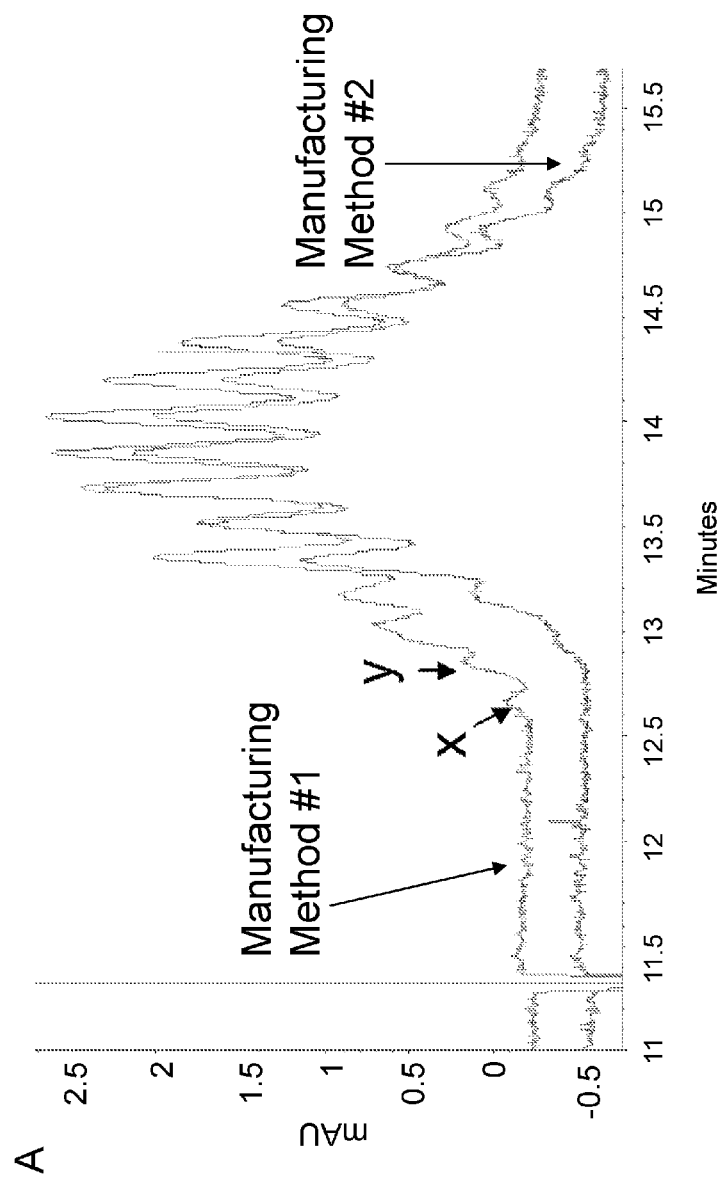
FIGS. 13A & 13B. depicts the charge profile for recombinant HNS enzyme produced using two different manufacturing processes, analyzed by (13A) capillary zone electrophoresis to determine (13B) the relative peak area (%) for the different HNS charge isoforms. Labels X and Y denote the presence of additional peaks outside the previously identified 14 isoforms.
Figure 13B:
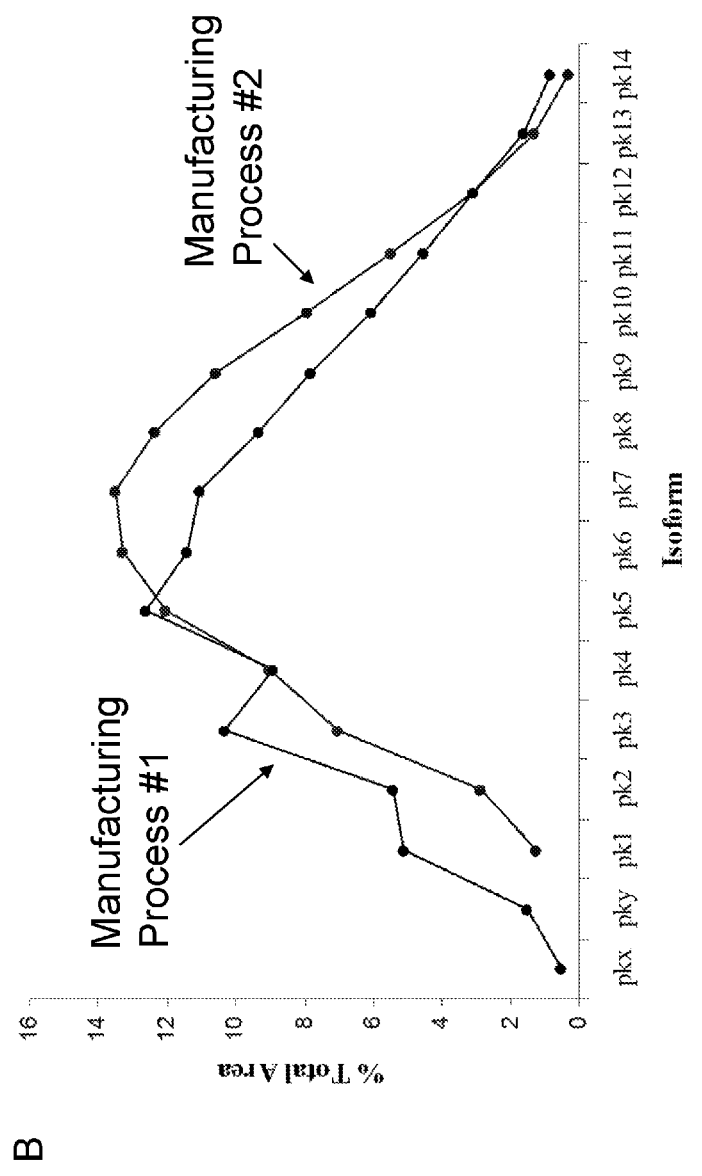

FIG. 13A shows the overlaid electropherograms of each manufactured HNS sample (Manufacturing Method #1 and Manufacturing Method #2). The data demonstrates, that minor deviations in the HNS manufacturing process can result in observable differences in the native charge profile. In particular, manufacturing method 1, resulted in a different isoform population, with two additional negatively charged peaks (indicated as "X" and "Y") in FIG. 13A; and in FIG. 13B as "pkx" and "pky" when graphed according to the calculated relative peak area (represented as percent total area). These quantifiable differences were expressed by comparing the calculated relative peak area for each differently manufactured sample (Man. Pro. 1 and Man. Pro. 2), to characterized reference manufactured Lot 189 (FIG. 7) and displayed in Table 8.

TABLE 8

Comparison of Relative Peak Areas (%) for HNS Produced By Different Manufacturing Processes

| Isoform | Run 2 | | Run 3 | |
|---|---|---|---|---|
| | Ref. Man. | Man. Pro. 1 | Ref. Man. | Man. Pro. 2 |
| Iso-x | nd | 0.5 | nd | nd |
| Iso-y | nd | 1.5 | nd | nd |
| Iso-1 | 1.2 | 5.1 | 1.2 | 1.0 |
| Iso-2 | 2.9 | 5.4 | 2.8 | 2.7 |
| Iso-3 | 7.1 | 10.3 | 7.0 | 6.7 |
| Iso-4 | 9.0 | 8.9 | 8.8 | 8.8 |
| Iso-5 | 12.0 | 12.6 | 12.1 | 11.2 |
| Iso-6 | 13.3 | 11.4 | 13.1 | 12.7 |
| Iso-7 | 13.5 | 11.0 | 13.6 | 13.0 |
| Iso-8 | 12.3 | 9.3 | 12.3 | 12.1 |
| Iso-9 | 10.6 | 7.8 | 10.5 | 10.7 |
| Iso-10 | 7.9 | 6.1 | 8.1 | 8.6 |
| Iso-11 | 5.5 | 4.5 | 5.5 | 6.1 |
| Iso-12 | 3.1 | 3.1 | 3.1 | 3.9 |
| Iso-13 | 1.3 | 1.6 | 1.3 | 1.8 |
| Iso-14 | 0.3 | 0.8 | 0.5 | 0.8 |

Reference Manufacturing Process (Ref. Man.), Manufacturing Process #1 (Man. Pro. 1) and Manufacturing Process #2 (Man. Pro. 2)

Example 5. Glycan Profile of Recombinant HNS

Figure 14A:
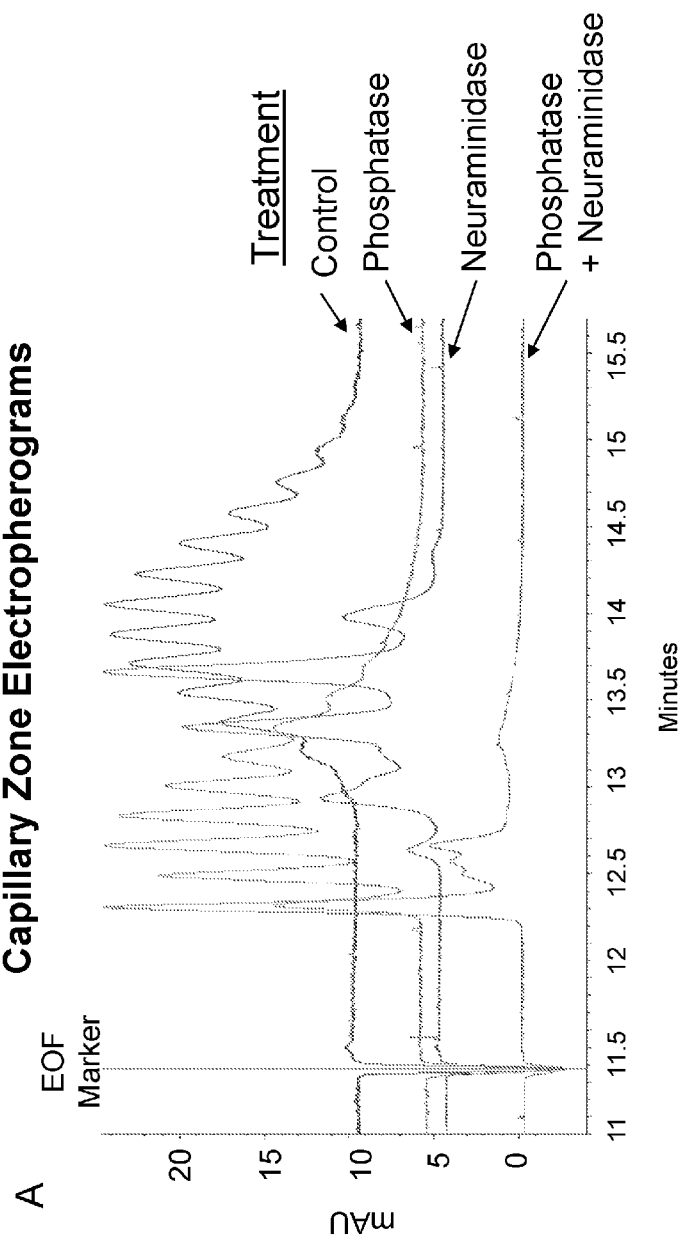
FIGS. 14A & 14B. depicts the glyco-characterization of recombinant HNS charge heterogeneity. (14A) Recombinant HNS was pre-treated with either phosphatase, neuraminidase, both, or no treatment control and then analyzed by capillary zone electrophoresis. (14B) Glycans released were analyzed by high performance anion-exchange chromatography with pulsed amperometric detection, producing a glycan map for total N-glycan analysis.
Figure 14B:
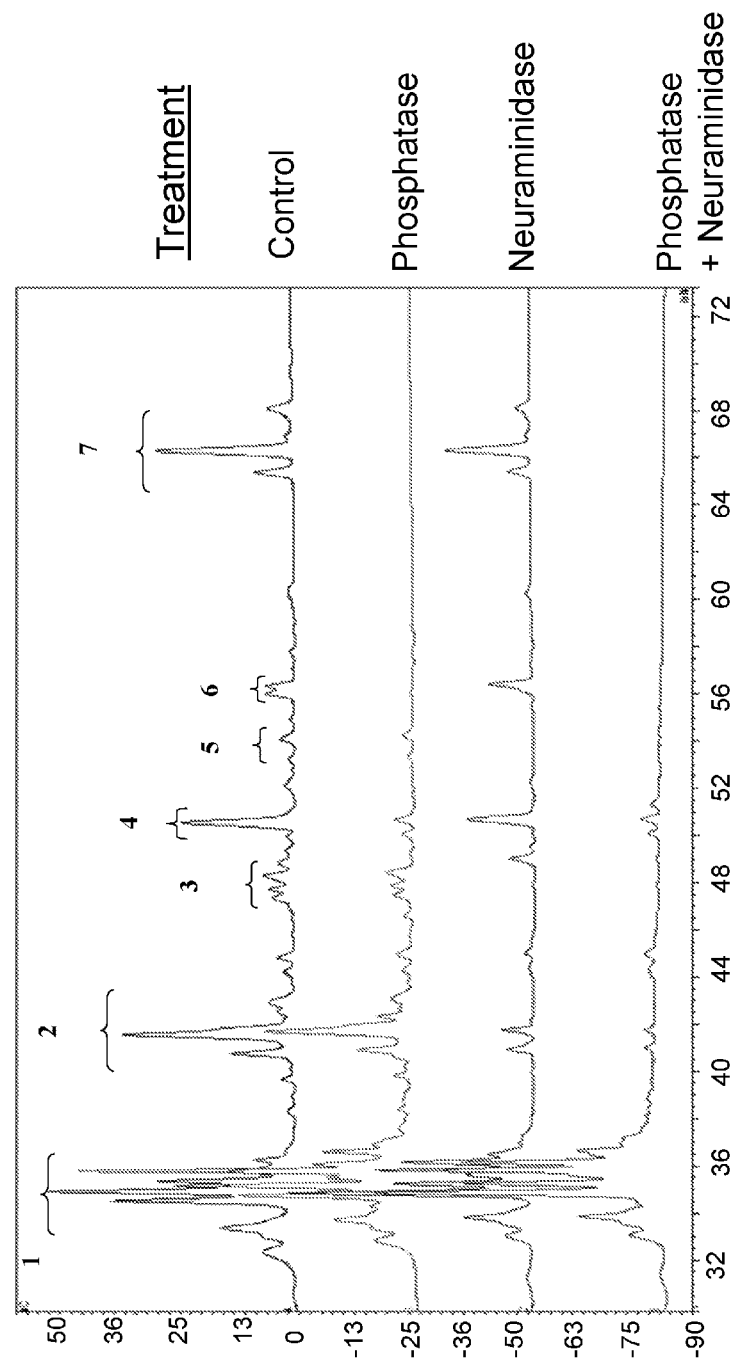

To determine if the basis for charge heterogeneity observed was due to glycosylation, CZE was performed, on samples pre-treated with the enzymes neuraminidase and/or phosphatase that release sialic acid and phosphate respectively (FIG. 14). Treatment with a combination of both enzymes significantly reduced the complexity of the electropherogram, with a predominant peak and several minor peaks all shifting closer towards the EOF marker, which is expected due to removal of negative charge.

Next, a condensed glycan map was generated for recombinant HNS. For the experiment, HNS protein was denatured at 100° C. for 3-4 min in the presence of 0.5% SDS, followed by enzymatic release of glycans with N-glycosidase F (Prozyme, San Leandro, Calif.). HNS samples were incubated with N-glycosidase F (30 mU/3 µL) for 4-6 h at 37° C. with 0.9% NP40, followed by a second addition of N-glycosidase F, and an additional 17-19 h incubation at 37° C. Separation of the released glycans was performed by high performance anion-exchange chromatography with pulsed amperometric detection (HPAE-PAD), using a CarboPac PA-1 analytical column equipped with a CarboPac PA-1 guard column (Dionex, Sunnyvale, Calif.). Glycans were applied to the column in 12 mM sodium acetate/100 mM NaOH, followed by elution with a 12-300 mM sodium acetate gradient (6.4 mM/min) in 100 mM NaOH in 45 min. Using a flow rate of 1 mL/min and the column at ambient room temperature. Glycans elute in the order of increasing charge characteristics and are classified into seven distinct peak groups. For human recombinant HNS, peak group 1 consists of all uncharged glycans, and peak groups 2, 3, and 5 consist of mono-, di-, and tri-sialylated glycans, respectively. The carbohydrate structures present in peak groups 4 and 7 are glycans with mono- and di-M6P groups, respectively. Peak group 6 consists of hybrid glycans containing both sialic acid and M6P. The presence of additional minor peaks in the glycan map is likely due to incomplete removal of either sialic acid and/or phosphate residues. These findings strongly suggest that the basis for the native charge heterogeneity seen by CZE is due to differences in both sialic acid and M6P content.

Experiments were also performed to evaluate two different lots of HNS produced using divergent manufacturing methods, which were previously show to have a different native charge isoform profile (FIG. 15A). For the experiment, glycan analysis was carried out to confirm that the difference in charge isoform profile observed, was due to differences in both sialic acid and M6P content. For the experiment, HNS protein from two different manufacturing processes (Process #1 and Process #2) were denatured at 100° C. for 3-4 min in the presence of 0.5% SDS, followed by enzymatic release of glycans with N-glycosidase F (Prozyme, San Leandro, Calif.). HNS samples were incubated with N-glycosidase F (30 mU/3 µL) for 4-6 h at 37° C. with 0.9% NP40, followed by a second addition of N-glycosidase F, and an additional 17-19 h incubation at 37° C. Separation of the released glycans was performed by high performance anion-exchange chromatography with pulsed amperometric detection (HPAE-PAD), using a CarboPac PA-1 analytical column equipped with a CarboPac PA-1 guard column (Dionex, Sunnyvale, Calif.). Glycans were applied to the column in 12 mM sodium acetate/100 mM NaOH, followed by elution with a 12-300 mM sodium acetate gradient (6.4 mM/min) in 100 mM NaOH in 45 min. Using a flow rate of 1 mL/min and the column at ambient room temperature. FIG. 15 demonstrates that the isoform charge profiles observed following enzymatic digest (FIGS. 15 B, C and D) was similar for both Process 1 and Process 2 samples. This suggests that any variation observed in the initial native charge isoform profile seen by CZE, was due to differences in both sialic acid and M6P content.

I claim:

1. A method of manufacturing a heparan N-sulfatase (HNS) protein comprising a step of analyzing a HNS protein manufactured at a large scale by capillary zone electrophoresis, wherein the analyzing step comprises characterizing the charge profile of the HNS protein.

2. The method of claim 1, further comprising a step of adjusting a manufacturing condition based on the analysis of the charge profile.

3. The method of claim 1, wherein the analyzing step is conducted before releasing a manufacturing lot.

4. The method of claim 1, wherein characterizing the charge profile comprises a step of separating peak groups indicative of absence or presence of charge variants by capillary zone electrophoresis.

5. The method of claim 1, wherein the charge profile comprises at least 14 peak groups.

6. The method of claim 4, wherein the charge variants are associated with the absence, presence of varying amounts of sialic acid and/or M6P groups.

7. The method of claim 4, wherein the charge variants are associated with the absence, presence of varying amount of mono-, di-, tri-sialylated glycans, mono-, di-M6P groups, and combination thereof.

8. The method of claim 1, wherein the characterizing step comprises quantitatively determining relative migration time and/or relative peak area of each peak group.

9. The method of claim 8, wherein the relative migration time of each peak group is determined relative to an electroosmotic flow (EOF) marker.

10. The method of claim 8, wherein the relative peak area of each peak group is calculated by peak area percentage as compared to the total peak areas.

11. The method of claim 1, wherein the method further comprises determining the quality of the HNS protein.

12. The method of claim 1, wherein the HNS protein is produced by mammalian cells.

13. The method of claim 12, wherein the mammalian cells are human cells.

14. The method of claim 1, wherein the method comprises determining if there is variation in the charge profile of the HNS protein as compared to a reference.

15. The method of claim 14, wherein the reference is the charge profile of a HNS protein produced from a different manufacturing batch.

16. The method of claim 15, wherein the method further comprises a step of assessing batch-to-batch charge variability comprising comparing graphs trending the relative peak areas versus peak groups for each HNS protein produced by different batches.

17. The method of claim 1, wherein the capillary zone electrophoresis is conducted under conditions such that longer migration times correspond to species of increasing negative charges.

18. The method of claim 1, wherein the capillary zone electrophoresis is conducted using a buffer system comprising Tris at a concentration ranging from about 20-30 mM.

19. The method of claim 1, wherein the buffer system has a pH ranging from approximately 7.8-8.2.

20. The method of claim 1, wherein capillary zone electrophoresis is conducted using a capillary with a length ranging between 56-112.5 cm.

* * * * *